United States Patent
Armstrong et al.

(10) Patent No.: US 6,827,731 B2
(45) Date of Patent: Dec. 7, 2004

(54) DEPLOYMENT SYSTEM FOR INTRALUMINAL DEVICES

(75) Inventors: Joseph R. Armstrong, Flagstaff, AZ (US); Edward H. Cully, Flagstaff, AZ (US); Mark J. Ulm, Flagstaff, AZ (US); Michael J. Vonesh, Flagstaff, AZ (US)

(73) Assignee: Gore Enterprise Holdings, Inc., Newark, DE (US)

( * ) Notice: Subject to any disclaimer, the term of this patent is extended or adjusted under 35 U.S.C. 154(b) by 0 days.

(21) Appl. No.: 10/054,772

(22) Filed: Jan. 22, 2002

(65) Prior Publication Data
US 2002/0099431 A1 Jul. 25, 2002

Related U.S. Application Data

(63) Continuation-in-part of application No. 09/767,314, filed on Jan. 22, 2001, now abandoned.

(51) Int. Cl.$^7$ .................................................. A61F 2/06
(52) U.S. Cl. ..................................................... 623/1.12
(58) Field of Search ............................... 623/1.11, 1.12; 606/108

(56) References Cited

U.S. PATENT DOCUMENTS

| | | | |
|---|---|---|---|
| 4,878,906 A | 11/1989 | Lindemann et al. | ............ 623/1 |
| 5,019,085 A | 5/1991 | Hillstead | ..................... 606/108 |
| 5,405,378 A | 4/1995 | Strecker | ........................ 623/1 |

(List continued on next page.)

FOREIGN PATENT DOCUMENTS

| | | |
|---|---|---|
| EP | 0696447 | 2/1996 |
| EP | 1064888 | 1/2001 |
| FR | 2382228 | 9/1978 |
| GB | 1601691 | 11/1981 |
| WO | 9820812 | 5/1998 |
| WO | 9827894 | 7/1998 |
| WO | 99/65420 | 12/1999 |
| WO | 00/38754 | 6/2000 |
| WO | 00/62709 | 10/2000 |
| WO | 0124733 | 4/2001 |

OTHER PUBLICATIONS

Instructions For Use For: Excluder™ Bifurcated Endoprosthesis. W. L. Gore & Associates, Inc. Gore & Associates, Inc. 2002.

Primary Examiner—Corrine McDermott
Assistant Examiner—Thomas J Sweet
(74) Attorney, Agent, or Firm—Wayne D. House

(57) ABSTRACT

A constraining sheath for use around an endoprosthesis (e.g., a stent device, with or without a graft covering), which may be a balloon expandable endoprosthesis but more preferably is a self-expanding prosthesis. The endoprosthesis is coaxially enclosed within the constraining sheath, which is an outer, disruptable, preferably implantable tubular sheath, preferably made of ePTFE. The constraining sheath and endoprosthesis are preferably mounted together as an assembly on an angioplasty balloon for delivery. Deployment of the endoprosthesis entails inflating the angioplasty balloon to a pressure sufficient to disrupt or break the constraining sheath in a prescribed fashion, thereby allowing a self-expanding endoprosthesis to spontaneously deploy. The constraining sheath of ePTFE may be attached to the endoprosthesis and implanted along with the device, or alternatively attached to the balloon catheter shaft and removed with the balloon catheter. The angioplasty balloon's working length is preferably shorter than the length of the endoprosthesis. An endoprosthesis assembly incorporating a constraining sheath according to one embodiment of the invention is also provided with an additional packaging sheath.

36 Claims, 21 Drawing Sheets

U.S. PATENT DOCUMENTS

| | | |
|---|---|---|
| 5,476,506 A | 12/1995 | Lunn ............................... 623/1 |
| 5,478,349 A | 12/1995 | Nicholas ...................... 606/198 |
| 5,524,757 A | 6/1996 | Andrews et al. ............. 206/438 |
| 5,755,769 A | 5/1998 | Richard et al. ................ 623/11 |
| 5,765,682 A | 6/1998 | Bley et al. ................... 206/363 |
| 5,919,225 A | 7/1999 | Lau et al. ....................... 623/1 |
| 5,948,191 A | 9/1999 | Solovay ........................ 156/86 |
| 6,019,787 A | 2/2000 | Richard et al. ................. 623/1 |
| 6,042,605 A | 3/2000 | Martin et al. ................... 623/1 |
| 6,048,360 A | 4/2000 | Khosravi et al. ............... 623/1 |
| 6,051,431 A * | 4/2000 | Selten et al. ................. 435/465 |
| 6,086,610 A | 7/2000 | Duerig et al. ................... 623/1 |
| 6,447,540 B1 * | 9/2002 | Fontaine et al. ........... 623/1.12 |
| 6,533,806 B1 * | 3/2003 | Sullivan et al. ............ 623/1.11 |
| 2002/0052640 A1 | 5/2002 | Bigus et al. ................ 623/1.11 |

\* cited by examiner

DEPLOYMENT SYSTEM FOR INTRALUMINAL DEVICES

CROSS REFERENCE TO RELATED APPLICATIONS

This application is a continuation-in-part of application Ser. No. 09/767,314 filed Jan. 22, 2001 now abandoned.

FIELD OF THE INVENTION

The present invention relates to the transcatheter delivery and remote deployment of implantable medical devices and more particularly implantable intraluminal devices of either the self-expanding type or the balloon expandable type.

BACKGROUND OF THE INVENTION

Endoluminal therapies typically involve the insertion of a delivery catheter that transports an implantable prosthetic device into the vasculature through a small, often percutaneous, access site in a remote vessel. Once access to the vasculature is achieved, the delivery catheter is used to mediate intraluminal delivery and subsequent deployment of the prosthesis via one of several techniques. In this fashion, the prosthesis can be remotely implanted to achieve a therapeutic outcome. In contrast to conventional surgical therapies, endoluminal treatments are distinguished by their "minimally invasive" nature.

Self-expanding endoprostheses are generally comprised of a stent component with or without a graft covering over the stent interstices. They are designed to spontaneous dilate (i.e., elastically recover) from their delivery diameter, through a range of intermediary diameters, up to a maximal, pre-determined functional diameter. The endoluminal delivery and deployment of self-expanding endoprostheses pose several unique problems. First, the endoprosthesis itself must be radially compacted to a suitable introductory size (or delivery diameter) to allow insertion into the vasculature, then it must be constrained in that compacted state and mounted onto a delivery device such as a catheter shaft. Subsequently, the constraint must be removed in order to allow the endoprosthesis to expand to its functional diameter and achieve the desired therapeutic outcome. Preferably, the means of constraint will not adversely affect the delivery catheter performance (e.g., detracting from the flexibility of the delivery system) or add significantly to introductory profile. The constraint must also incorporate some type of release mechanism or scheme that can be remotely actuated by the implanting clinician. Consequently, deployment methodologies that are consistent with conventional interventional practices are preferred.

Delivery mechanisms for self-expanding endoprostheses of the prior art may be generally classified into one of two general categories, either coaxial sheaths or fiber-based constraints. Delivery systems also exist that use both of these types of mechanisms.

Tubular coaxial sheaths are one approach used to constrain the compacted self-expanding endoprosthesis. Normally, these coaxial sheaths extend over the entire length of an inner delivery catheter onto which the endoprosthesis is mounted near the catheter tip (i.e., leading end). Deployment is typically initiated by pulling on a handle or knob located near the hub (i.e., trailing end) of the catheter, which retracts the constraining sheath and allows the device to expand. During this procedure, the clinician maintains the position of the device by holding the inner (delivery) catheter in a stationary position. Existing problems and/or complications with the tubular coaxial sheath type of delivery system include friction between compacted device and constraining sheath, friction between the constraining sheath and delivery catheter, and friction between the delivery catheter and constraining sheath hemostasis valve, all of which can hinder deployment accuracy, speed and control. Additionally, a tubular coaxial constraining sheath can also reduce flexibility and add introductory profile due to the thickness of the constraining sheath.

U.S. Pat. No. 6,086,610 to Duerig et al. teaches a self-expanding stent provided with a tubular constraining sheath that is plastically deformable by a circumferential distending force such as a catheter balloon. This sheath remains implanted with the stent following deployment and fully covers the entire circumference of the stent in the fashion of a conventional stent covering, i.e., the tubular sheath is not disrupted. The Duerig et al. device is delivered from a conventional balloon catheter, but thought to have limitations, including radial recoil of the sheath after the balloon is pressurized, which can compromise luminal gain. Further, the presence of the cover may adversely affect the ability of the stent to fully deploy, and the balloon length must be equal to or longer than the stent, and this long balloon can potentially damage the vessel.

In the fiber-based delivery systems, the self-expanding endoprosthesis is constrained in the delivery profile by one or more removable fibrous strands, with or without an additional implantable constraint element. The endoprosthesis is released from its compacted state through tension applied to a deployment "cord" that normally runs through an additional lumen within the delivery catheter. Typically, applying tension to the deployment cord initiates the release of the fiber constraint by unlacing linear slip knots (e.g., Lau, et al., U.S. Pat. No. 5,919,225), removing circumferential croquet knots (e.g., Strecker, U.S. Pat. No. 5,405,378), or detaching the interlocking loops of a warp-knitted constraint (e.g., Armstrong et al., WO99/65420). Other fiber-based delivery systems are described by Lindemann, U.S. Pat. No. 4,878,906, and Hillstead, U.S. Pat. No. 5,019,085.

Another variant of the fiber-based delivery systems is the mechanism employed in the EXCLUDER® endoprosthesis marketed by W. L. Gore and Associates, Inc (Flagstaff, Ariz.). This mechanism entails a "chain-stitch" sewn into the seam of a biocompatible constraining tube that contains the compacted endoprosthesis. Applying tension to the fibrous constraint in this mechanism allows the seam in the biocompatible constraining tube to be open, and the self-expanding endoprosthesis to deploy. The biocompatible constraining tube is implanted along with the endoprosthesis, trapped between the abluminal surface of the device and the wall of the host vessel. See WO98/27894.

U.S. Pat. Nos. 5,755,769 and 6,019,787 to Richard et al. teach another constraining sheath around a self-expanding stent. The sheath is cut longitudinally into several segments by cutting wires or fibers actuated by pulling a handle at the opposite end of the delivery system. The sheath is attached to or integral to the delivery catheter with the result that the segments are removed with the catheter following stent deployment. No catheter balloon or other means for exerting a circumferential disrupting force to the sheath is suggested, nor are materials appropriate for the sheath suggested. This design requires lines to run over the length of the catheter.

Problems with fiber-based type of delivery systems include possible premature deployment during introduction to the vascular system through hemostasis valves, extra lumens required on the delivery catheter which can increase profile, possible snagging of fiber(s) on the compacted implantable device, the possibility of emboli resulting from moving lines between the catheter and the blood vessel, and possible breakage of the deployment cord itself.

SUMMARY OF THE INVENTION

The present invention relates to a constraining sheath for use around an endoprosthesis (e.g., a stent device, with or without a graft covering), which may be a balloon expandable endoprosthesis but more preferably is a self-expanding prosthesis. The endoprosthesis is enclosed within the constraining sheath which is an outer, disruptable, preferably implantable tubular sheath which is preferably made of porous expanded polytetrafluoroethylene (hereinafter ePTFE, made as generally taught by U.S. Pat. Nos. 3,953, 566 and 4,187,390 to Gore). The constraining sheath is characterized by having means for disruption such as a row of perforations or a seamline, with disruption of the constraining sheath and release of the endoprosthesis (resulting in expansion and deployment of the endoprosthesis) initiated by a distending force applied to the containment sheath. Preferably, disruption of the constraining sheath entails interruption of the continuity of the circumference of the constraining sheath, for example, as by tearing of a row of perforations.

The constraining sheath and endoprosthesis are mounted together as an assembly on an angioplasty balloon for delivery. Preferably, deployment of the endoprosthesis entails inflating the angioplasty balloon to a pressure sufficient to disrupt or break the constraining sheath in a prescribed fashion, thereby allowing a self-expanding endoprosthesis to spontaneously deploy. The catheter balloon thus supplies the necessary distending force to initiate disruption of the constraining sheath.

The constraining sheath is preferably attached to the endoprosthesis and is implanted along with the device. In this fashion, a self-expanding endoprosthesis can be deployed using methodologies and procedural techniques identical to those routinely employed for the implantation of balloon-expandable endoprostheses.

A self-expanding endoprosthesis can also be used to advantage to provide the necessary distending force (i.e., without requirement for a catheter balloon) if an alternative mechanism is supplied to enable disruption of the constraining sheath. Additionally, if a balloon is employed, the balloon's inflated diameter under at least a length of the self-expanding endoprosthesis may be smaller than the intended deployed diameter of the endoprosthesis, yet large enough to initiate disruption or breaking of the constraint.

The phrase "stent graft" is used herein to describe a stent provided with a covering, typically of a vascular graft material such as ePTFE or polyethylene terephthalate. The covering may be provided over either or both of the inner and outer surfaces of the stent. The covering may cover a portion of the otherwise open stent interstices or it may cover all of the stent interstices.

With regard to either a self-expanding or a balloon expandable endoprosthesis, the constraining sheath may be employed to provide a smoother and more lubricious exterior surface during delivery than would be possible with a balloon expandable stent that would otherwise present a relatively rough exterior surface to the lumen of the blood vessel into which it is inserted.

The breakaway constraining sheath of the present invention overcomes many of the disadvantages of the previously described delivery systems and establishes numerous unique advantages. The sheath of the present invention, particularly when made of ePTFE, has a much smoother, continuous outer surface than the fiber-based systems, which may reduce the incidence of iatrogenic endothelial traumatization. It may be used to deploy a device beginning at the tip end and progressing to the hub end (i.e., distal end to proximal end), or hub end to tip end, or both ends toward the middle, or middle to both ends. The constraining sheath when made of a preferred ePTFE material may be provided with an extremely thin wall thickness (adding only 0.025–0.050 mm to total introductory profile) while providing extremely high strength. This enables substantial diametrical compaction of the device. The ePTFE sheath can allow almost immediate tissue ingrowth due to its inherent porous microstructure and thereby assist in anchoring the endoprosthesis. The sheath can be affixed to the exterior of an endoprosthesis, or alternatively can be provided without direct attachment to the endoprosthesis.

The constraining sheath can be configured to secure the endoprosthesis to the underlying delivery system. This may be accomplished by releasably attaching portions of the constraining sheath to the dilatation balloon or to the dilatation balloon catheter.

The deployment mechanism mimics the procedural techniques used with popular balloon-expandable endoprostheses and thus will require minimal user training. The flexibility of the delivery system is minimally compromised, which is important for device delivery through tortuous anatomy. Reliability of deployment may be improved. There is a high degree of confidence in deployment reliability since this constraint is not compromised by subsequent stitching or the use of pull strings, rip-cords or deployment lines, creep of constraints, overcoming high static frictional forces, etc. Since the sheath is provided over an endoprosthesis mounted on the angioplasty balloon, this system affords the opportunity for "primary stenting," that is, device implantation without preceding balloon dilatation of the host vessel. If primary stenting proves feasible for the particular patient, fluoroscopy time may be reduced (reducing the exposure of both patient and clinician to x-ray), as well as overall procedural time and expense. Risk of emboli formation may also be reduced. Additionally, once implanted, the self-expanding device is completely unconstrained, thereby allowing for compensatory remodeling (i.e., continued enlargement of the endoprosthesis over time).

The present invention provides a method of manufacture for the constraining sheath, and also relates to its assembly over a balloon catheter and an endoprosthesis. It also provides a means of controlling the radial dynamics of device deployment. For example, the present invention can be configured to 'pop' open to allow rapid device deployment, or alternatively to undergo more gradual, high strain yielding prior to disruption and device deployment, or a combination of both.

The present invention preferably includes one or more lines of perforations as a means to render the constraint disruptable in a prescribed fashion, the perforations being generally oriented along the longitudinal axis of the device. Alternative perforation patterns (e.g., helical, discontinuous, zigzag, etc.) are also possible.

Disruption of the inventive constraining sheath is possible via other methods, which typically involve creating a line or zone of weakness along the length of the sheath such as by the use of a lesser amount of material in the zone of weakness. Other methods of creating a zone of weakness may include the application of thermal or mechanical treatments to a localized region. Additionally, active elements such as spring components or elastic segments included with the sheath may be used to facilitate constraining sheath removal.

Embodiments of the present invention also allow removal of the external constraining sheath, following disruption, along with the delivery catheter. This may be accomplished by securing the hub or proximal end of the constraining sheath to the catheter and optionally providing the sheath with several parallel perforated seams.

The constraining sheath may be imbibed with various pharmaceutical, biological, or genetic therapies for targeted luminal delivery of these substances. Following deployment of the endoprosthesis, these therapeutic agents can be released over time. An advantage of this approach is that the loading of the sheath with any of these therapeutic agents can be performed independent of the endoprosthesis manufacture. Further, radiopaque elements may be incorporated into the constraining sheath to facilitate fluoroscopic visualization.

The present invention may also be used to deliver and deploy multiple, coaxially loaded devices.

The present invention preferably employs a balloon with a shorter inflated working length than that of the endoprosthesis. This configuration allows full deployment of the self-expanding endoprosthesis with the ability to dilate the mid-length of the endoprosthesis in one step. The shorter length balloon minimizes the risk of dilating healthy vessel tissue adjacent to the deployed endoprosthesis.

In a preferred embodiment, the constraining sheath can be made to be extremely thin, or "delicate," for minimal implantation profile. Such a delicate constraining sheath is not adequate, without further exterior support, to constrain the endoprosthesis assembly (particularly when the assembly includes a self-expanding endoprosthesis) for very long periods of time or for shorter periods when exposed to elevated temperatures. The use of such a delicate constraining sheath is made practically possible when the assembly is provided with an additional packaging sheath that prevents inadvertent disruption of the constraining sheath or undesirable increase in diameter of the assembly (in an amount of 0.15 mm or more). The packaging sheath is removed prior to implantation and accordingly is not required to be made of an implantable material or a material with a thin wall. Alternatively, the endoprosthesis assembly may incorporate such a delicate constraining sheath if it is stored at reduced temperatures, such as 5° C. or less, prior to implantation.

DETAILED DESCRIPTION OF THE INVENTION

Figure 1:
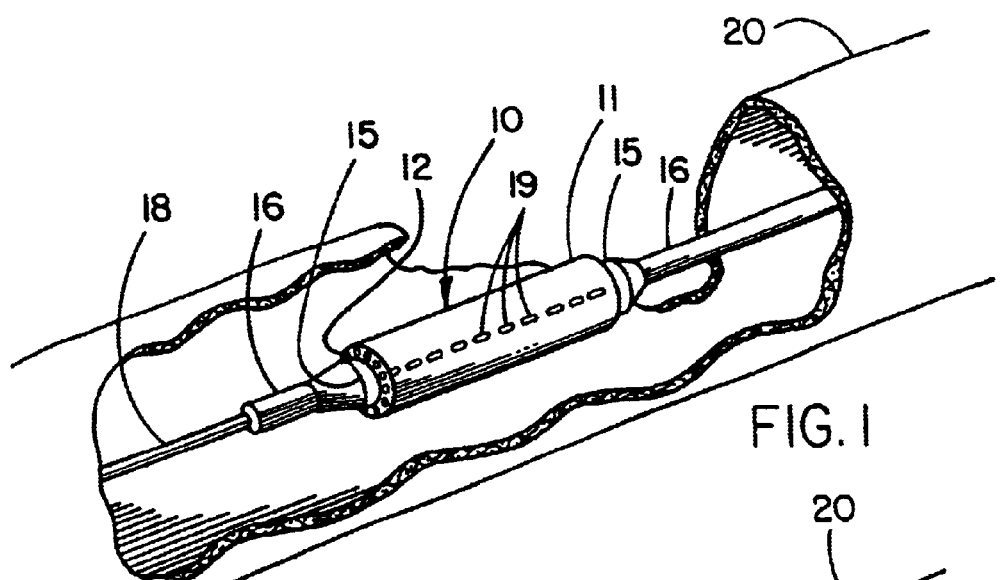
FIG. 1 describes a perspective view of the constraining sheath assembly of the present invention as inserted into a portion of a vascular system prior to deployment.

FIG. 1 shows a perspective view of the constraining sheath assembly 10 of the present invention wherein constraining sheath 11 is fitted about an endoprosthesis 12, balloon 15 affixed to a catheter 16, and guidewire 18, after insertion to a desired site within a body conduit 20 such as the vasculature. Endoprosthesis 12 is indicative of any type of medical device which might be usefully contained at a smaller diameter for insertion into a body conduit and subsequently deployed to a larger diameter at a desired location within a body conduit. The endoprosthesis may be a stent-graft having a stent component and a covering over some or all of the open interstices of the stent. The covering may be provided over either or both of the inner and outer surfaces of the stent. Alternatively, the stent may be provided without any covering.

Figure 1A:
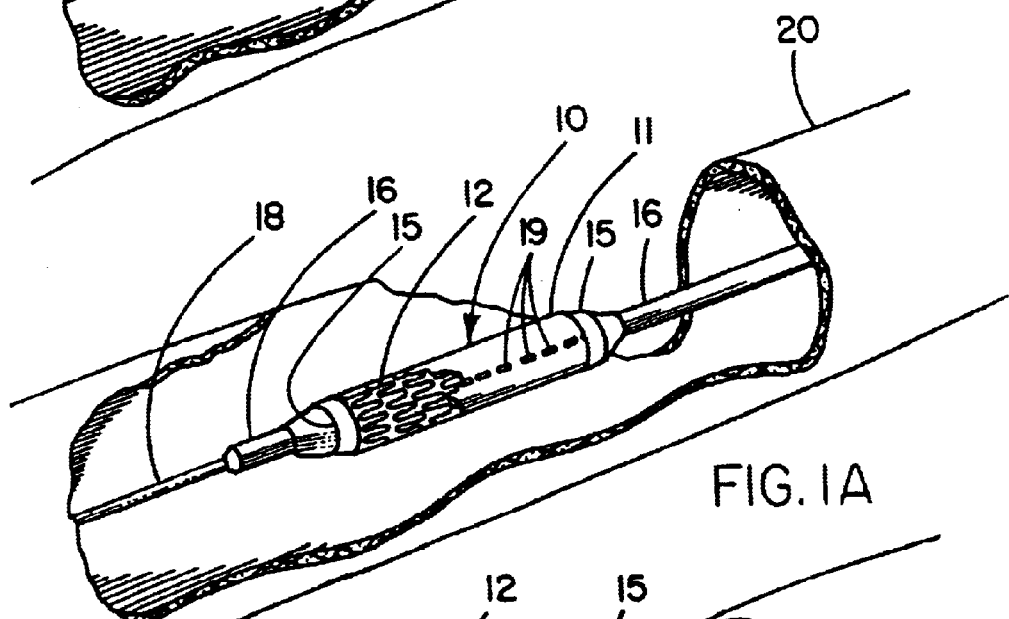
FIG. 1A describes a cutaway perspective view of the assembly of FIG. 1, with differing portions of adjacent components cutaway in order to allow description of all components.
Figure 1B:
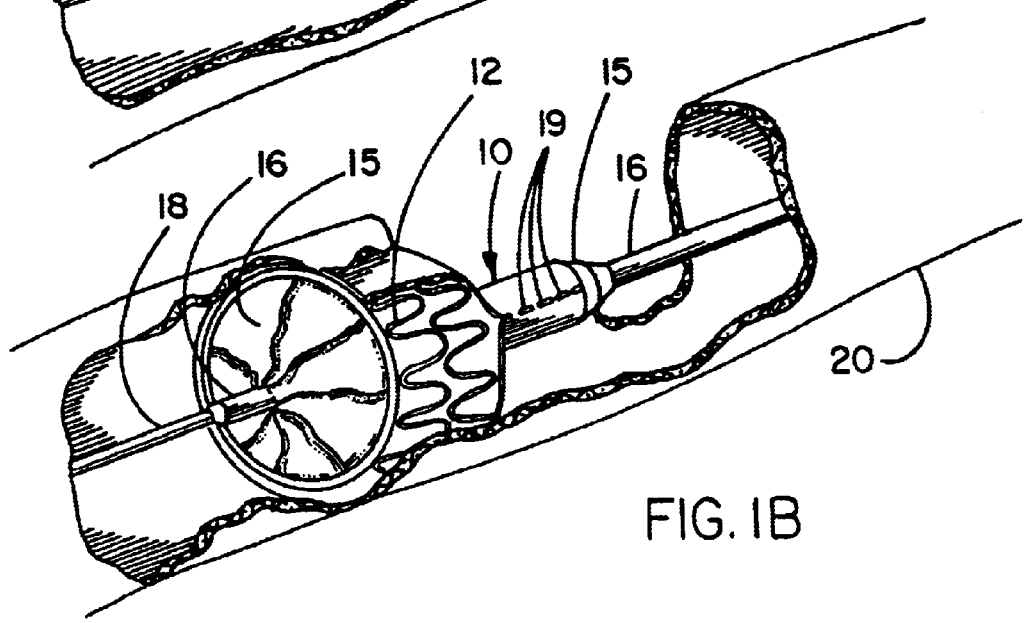
FIG. 1B describes a perspective view of the constraining sheath assembly during deployment, showing disruption of the constraining sheath.

FIG. 1A shows the same system in cutaway form for clarity of description of the various components. During deployment, as shown by the perspective view of FIG. 1B, the constraining sheath 11 is disrupted such as by tearing of a row of perforations 19 provided into the surface of sheath 11, with the result that the endoprosthesis 12 is freed of the constraining force and allowed to self-expand or to be expanded to a larger diameter. The disruption of the constraining sheath 11 is caused by inflation of the catheter balloon 15.

Figure 2:
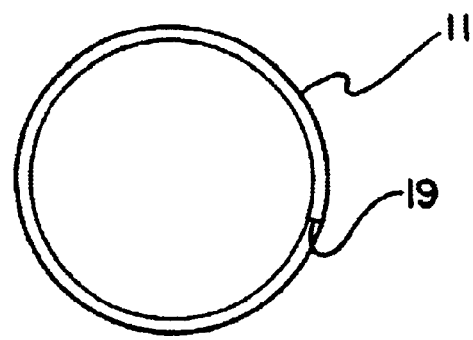
FIG. 2 describes a transverse cross section of a constraining sheath of the present invention.
Figure 2A:
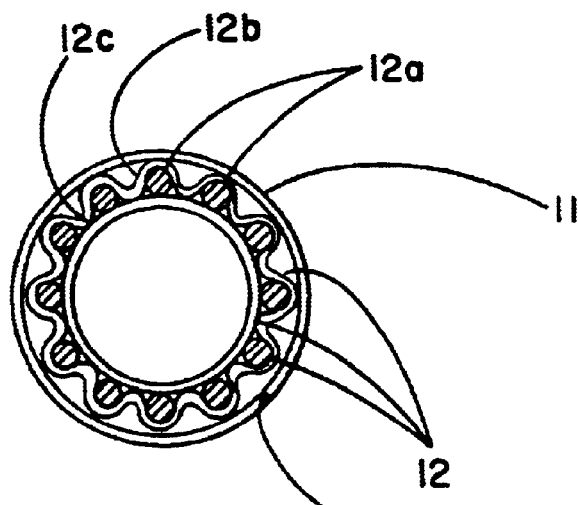
FIG. 2A describes a transverse cross section of a stent graft enclosed by a constraining sheath of the present invention prior to insertion into a vascular system.
Figure 2B:
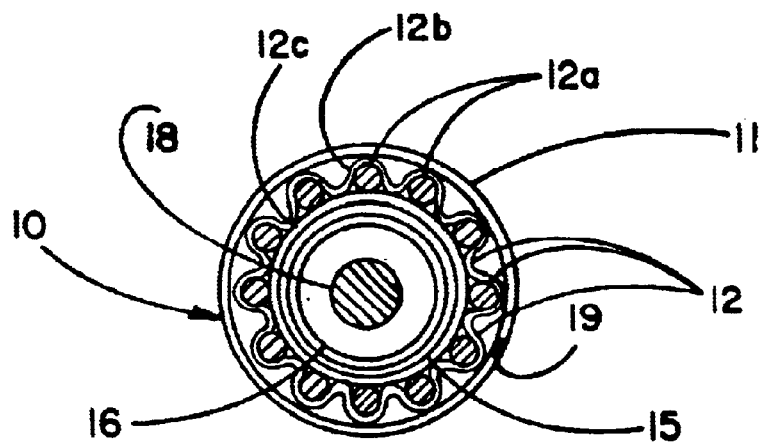
FIG. 2B describes a transverse cross section of the stent graft and constraining sheath of FIG. 2A with a balloon and guidewire fitted into the hollow lumen of the stent graft.

FIG. 2 describes a transverse cross section of a constraining sheath of the present invention, while FIG. 2A shows a transverse cross section of an endoprosthesis enclosed by a constraining sheath of the present invention prior to insertion into a vascular system. All transverse cross sections described herein may be considered to be taken at about the middle of the length of the constraining sheath assembly 10 or endoprosthesis 12. In the embodiment described by FIG. 2A, endoprosthesis 12 is a stent-graft in the form of a stent 12a provided with an outer covering 12b and an inner covering 12c, wherein both coverings are preferably ePTFE. FIG. 2B describes a transverse cross section of the stent graft and constraining sheath of FIG. 2A with a balloon and guidewire fitted into the hollow lumen of the stent graft.

Figure 3:
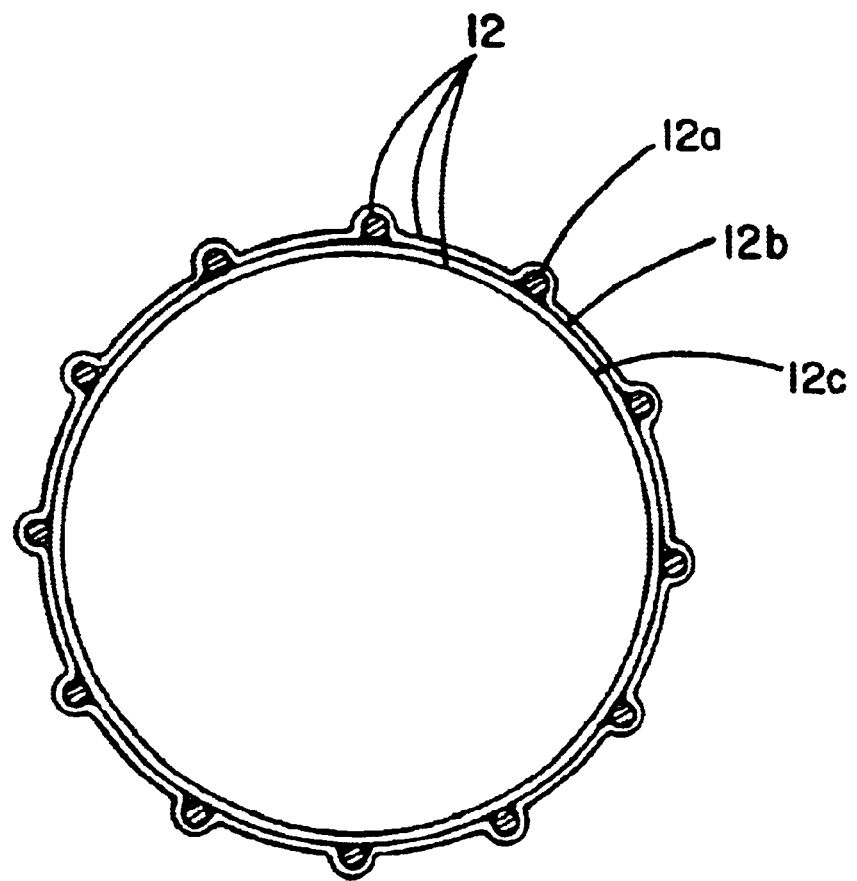
FIG. 3 is a transverse cross section of a typical stent graft in a fully deployed (i.e., maximum diameter) configuration.

FIG. 3 shows a transverse cross section of a typical endoprosthesis 12 of the prior art that has been deployed, that is, expanded from its smaller insertion diameter to a larger diameter that is intended to cause it to firmly contact the inner walls of a body conduit such as an artery. In the embodiment shown, the endoprosthesis comprises a stent 12a provided with outer 12b and inner 12c coverings.

Figure 3A:
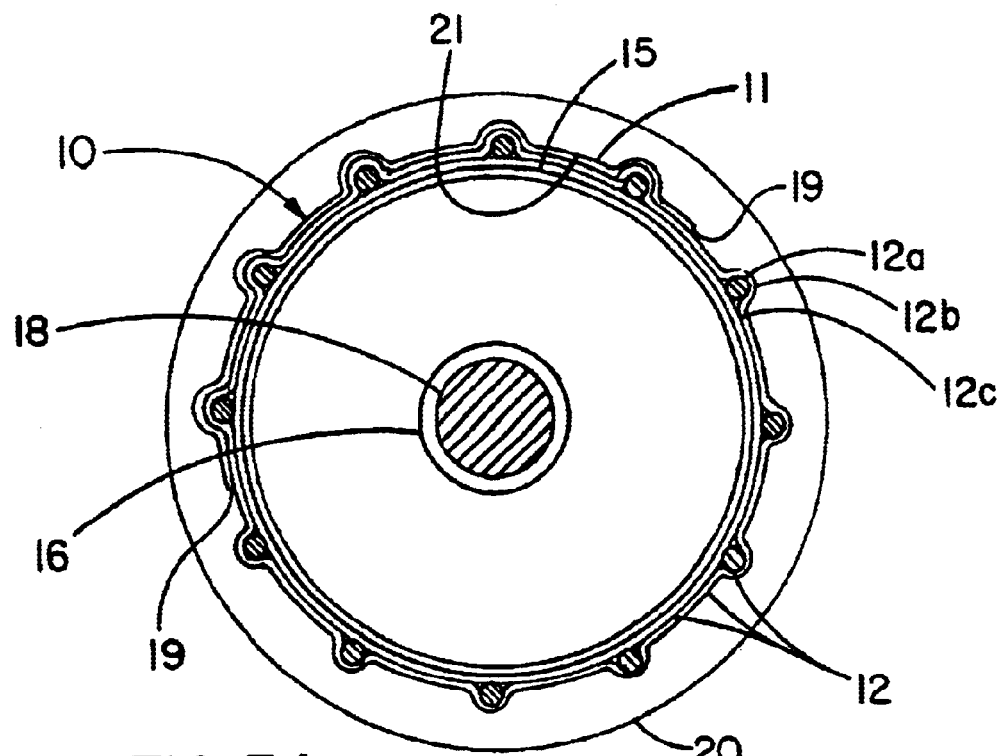
FIG. 3A is a transverse cross section of a stent graft with the constraining sheath of the present invention immediately after deployment while the balloon catheter is fully inflated.
Figure 3B:
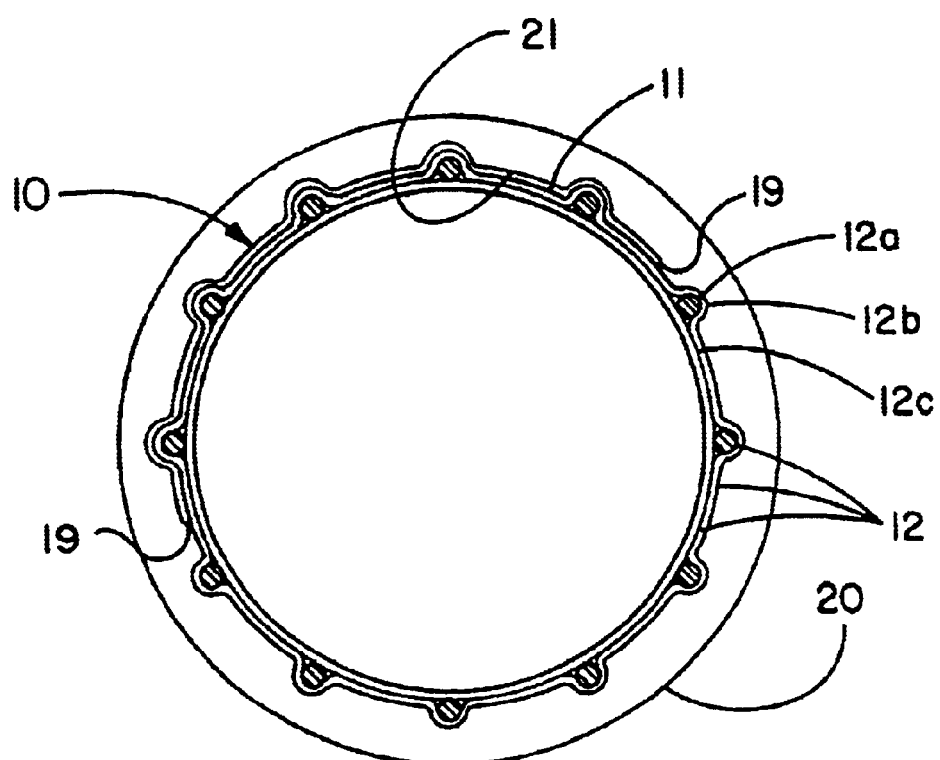
FIG. 3B is a transverse cross section of the deployed stent graft shown by FIG. 3A, following removal of the balloon catheter and guidewire.

FIG. 3A describes a transverse cross section of one embodiment of the constraining sheath assembly 10 of the present invention following deployment in a desired body conduit 20. Constraining sheath 11 is now disrupted and, following deployment of the endoprosthesis 12 to the desired larger diameter by balloon 15 (shown inflated) at the desired location within the body conduit 20, is located between the outer covering 12a of the stent graft and the luminal surface 21 of the body conduit 20. As made of ePTFE in the preferred embodiment, the disrupted sheath 11 is of minimal thickness and is highly biocompatible, with the result that it does not interfere with the function of the deployed endoprosthesis. Preferably, sheath 11 is physically attached to the outer surface of the endoprosthesis 12 along a line parallel to the longitudinal axis of the endoprosthesis and located approximately opposite the line of perforations. The transverse cross section of FIG. 3B describes the deployed endoprosthesis following deflation of balloon 15 and withdrawal of balloon 15 and guidewire 18, again showing the constraining sheath 11 remaining implanted between the body conduit 20 and the endoprosthesis 12.

Figure 4A:
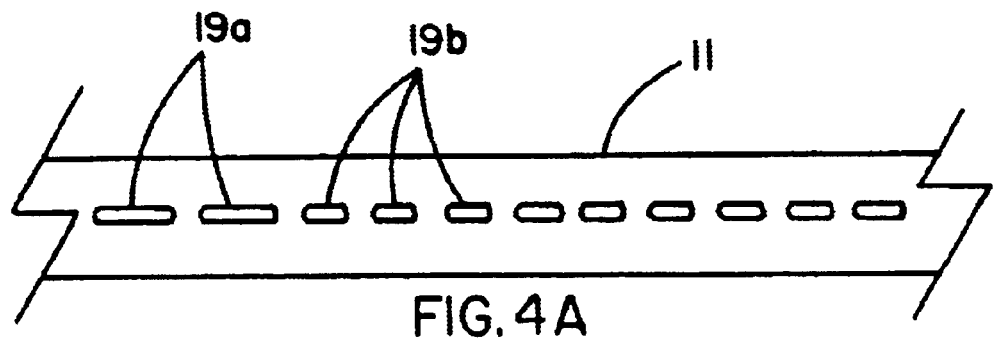
FIGS. 4A–4D show various alternative perforation designs for the constraining sheath of the present invention.
Figure 4B:
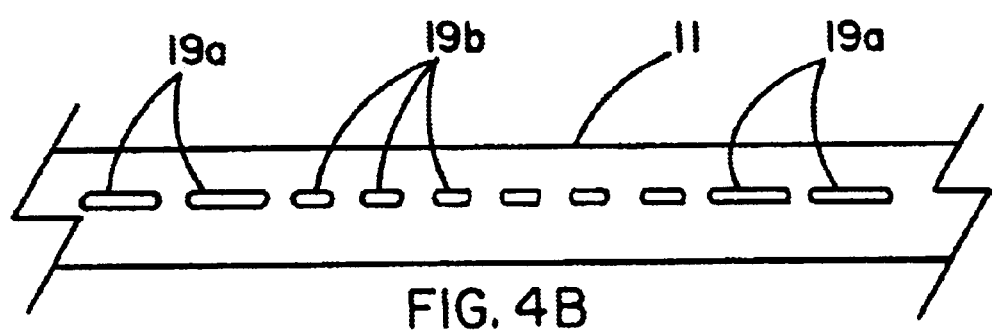
Figure 4C:
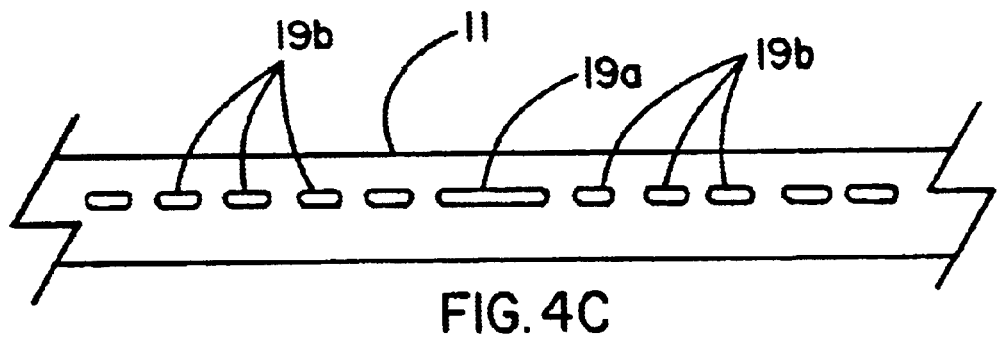
Figure 4D:
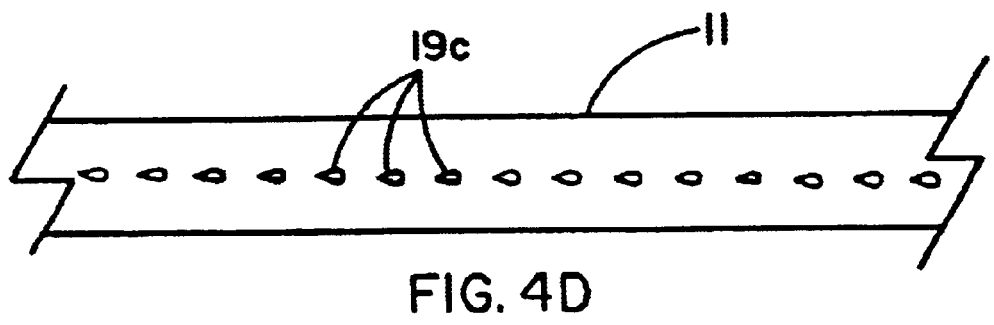

Perforations 19 are the preferred method of disrupting the constraining sheath as rupture of the sheath along the line of perforations can be easily controlled. The perforations can be varied in shape (e.g., length, width, spacing or the actual shape of an aperture), or arranged in various patterns other than a straight line. Individual perforations can be provided with different shapes, for example, if it is desired to have the disruption begin at a particular location on the sheath such as at a particular end of the sheath. FIGS. 4A–4C describe various perforation arrangements intended to control where disruption begins. FIG. 4A shows an arrangement where a particular end of the sheath 11 is provided with longer perforations 19a while the remainder of the length is provided with shorter perforations 19b in order to cause disruption to begin at the end with longer perforations 19a. Disruption can be caused to begin at either end as shown by the location of longer perforations 19a in FIG. 4B. FIG. 4C describes an embodiment wherein longer perforations 19a are provided in the middle of the length of the sheath 11 to cause disruption to begin at the middle of the length. FIG. 4D shows still another possibility wherein perforations 19c are provided of asymmetric shape in order to cause disruption to progress from a particular end of the sheath 11 to the opposite end.

Figure 5A:
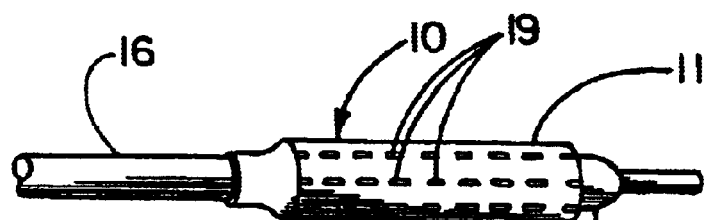
FIGS. 5A–5D show various alternative perforation designs for the constraining sheath of the present invention having the perforations in patterns other than a single continuous straight line.
Figure 5B:
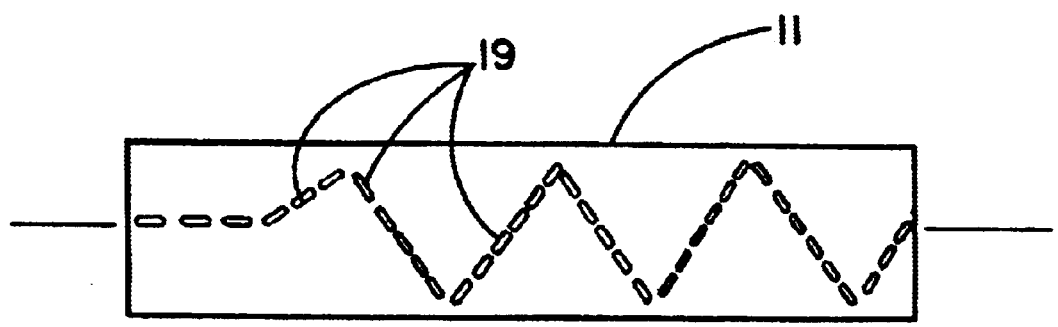
Figure 5C:
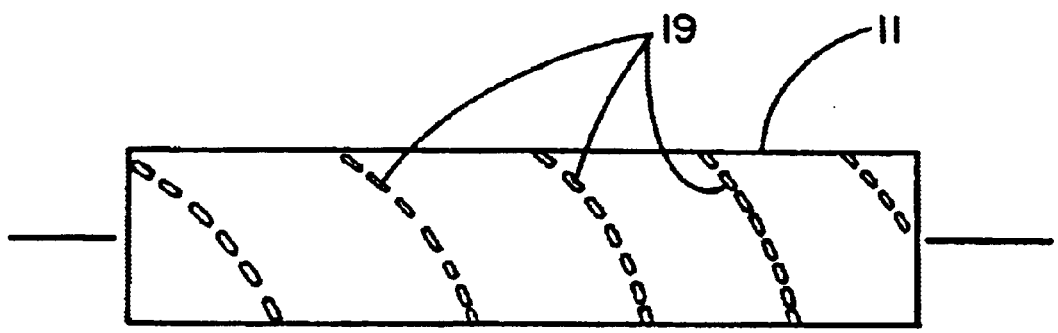
Figure 5D:
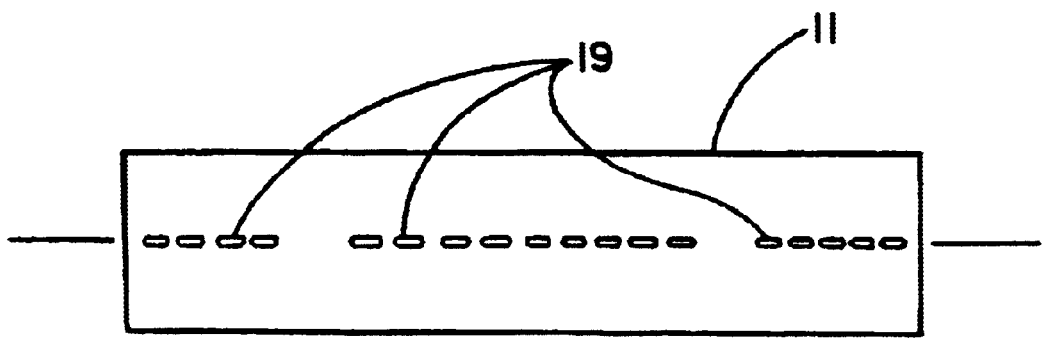

As described by FIGS. 5A–5D, the perforations 19 can be provided in arrangements of other than a single straight line. FIG. 5A shows multiple straight lines, which can result in the sheath 11 disrupting into multiple segments. Between each perforation it is preferred that the constraint is firmly attached to the endoprosthesis to facilitate disruption of the multiple perforations around the circumference. FIGS. 5B–5D describe other perforation arrangements such as non-straight lines if it is desired to have the sheath 11 disrupt into a shape with straight longitudinal edges.

Figure 6A:
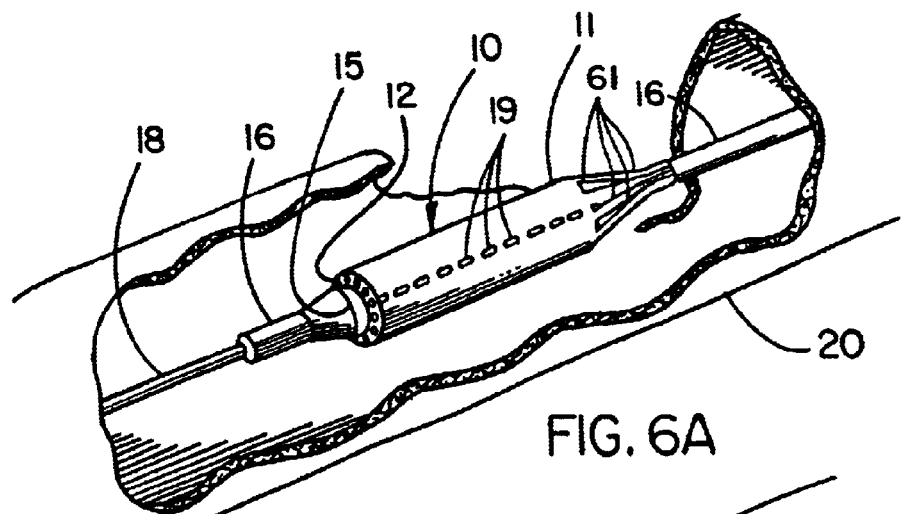
FIGS. 6A and 6B show sequential side views of an embodiment wherein the constraining sheath is removable with the catheter following deployment.
Figure 6B:
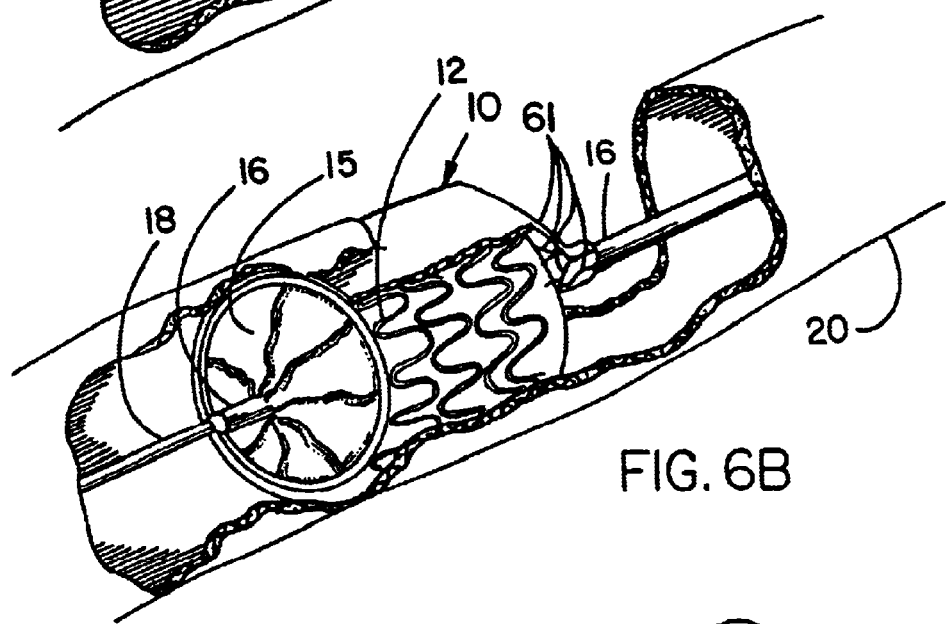

FIGS. 6A and 6B show an alternative embodiment wherein one end of the sheath is well affixed to the outer surface of the catheter 16 by extension strands 61. These strands may be integral with the constraining sheath 11 as shown or may be provided as separate components affixed to the sheath as well as to the catheter shaft 16. Following disruption of the sheath 11 and deployment of the endoprosthesis 12 as described by FIG. 6B, the sheath 11, being affixed at the proximal end to the catheter shaft 16, may be withdrawn along with the catheter 16. In addition to being well secured to the catheter shaft, the sheath must be made of a material of adequate tensile strength and should also be both thin and lubricious. ePTFE is a preferred material for this sheath application.

Figure 7:
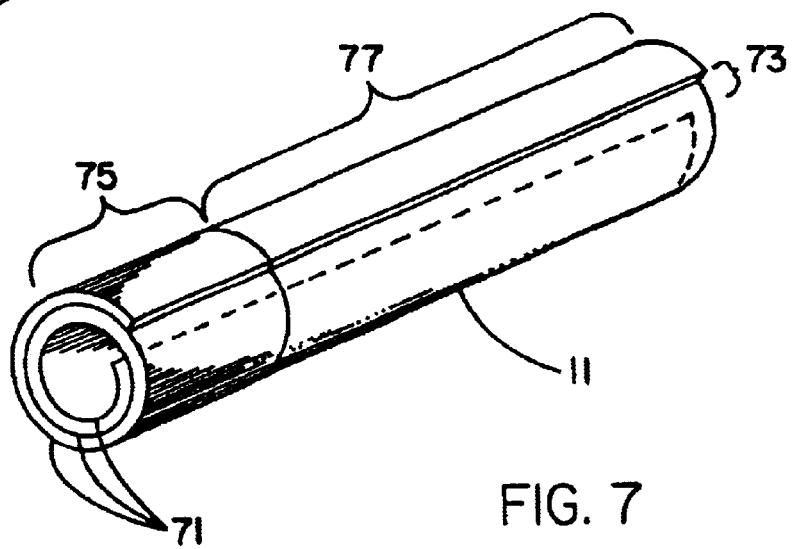
FIG. 7 is a perspective view of an alternative embodiment of a disruptable constraining sheath, wherein a narrow radial portion of the wall of the device is provided with a lesser amount of material as a means of disruption.

The disruption mechanism may be provided by means other than perforations. For example, FIG. 7 describes a tube made from layers of ePTFE film 71 such as uniaxially expanded films (expanded on only one direction or expanded substantially more along the length of the film than transversely); such films are taught by U.S. Pat. Nos. 3,953,566 and 4,187,390 to Gore. Another suitable film is a porous laminate of ePTFE and fluorinated ethylene propylene (FEP) made as taught by U.S. Pat. No. 6,025,044 to Campbell, et al. The film is wrapped around a mandrel (which may be provided with a suitable release layer if deemed necessary), typically with the fibrillar orientation of the film microstructure oriented parallel to the longitudinal axis of the mandrel. Typically (although not always), uniaxially expanded or predominantly uniaxially expanded ePTFE films will split in a direction parallel to the fibrils under application of relatively low, transversely applied force. The intent is to orient the direction of easy splitting to be parallel to the axis of the constraining sheath. The film is wrapped with less than full 360 degree wraps, for example, 2¾ revolutions, with the result that 90 degrees of revolution of the mandrel are provided with only 2 layers of film while the other 270 degrees of revolution are provided with 3 layers. The result is a thin tube having a region of reduced thickness 73, or a zone of weakness, along its length that serves as the means for prescribed disruption and can appropriately be used as a constraining sheath of the present invention. Such a tube will predictably disrupt along the, for example, 90 degree segment of the tube construct that has one less layer of film.

If the constraining tube is desired to disrupt from one particular end 75, then the opposite end 77 can be provided with an additional layer of film. For example, for the tube described immediately above, the full length of the tube can be provided with 2¾ layers, after which a majority of the length of the tube (e.g., ¾ of the length) can be provided with an additional layer so that it has 3¾ layers. The resulting constraining sheath will disrupt beginning at the end having less film and then propagate along a line proceeding longitudinally along the thinner portion of the tube wall.

Figure 8:
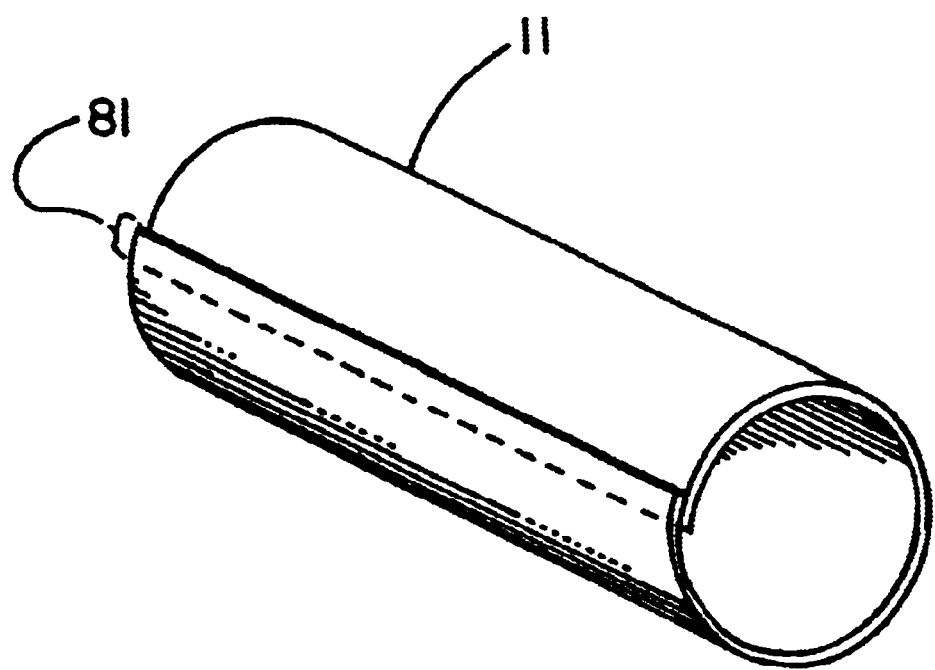
FIG. 8 is a perspective view of an alternative embodiment wherein the disruptable constraining sheath comprises a sheet rolled to form a tube with opposing edges of the sheet overlapped to form a lapjoint which is weaker than the remainder of the tube and thereby allows for disruption.

FIG. 8 describes still another embodiment of the constraining sheath wherein the sheath is made from a sheet rolled to form a tubular shape and provided with a seamline 81 resulting from the joining of opposite edges. The edges may be joined in abutting fashion or more preferably as shown by FIG. 8, in overlapping fashion. The edges are joined by any of various methods including the use of adhesives or by melt-bonding either the material of the sheath or a meltable adhesive. A suitable meltable adhesive for use with a constraining sheath of ePTFE is FEP. The joining is accomplished in a manner that results in the seam being weaker than the remainder of the material comprising the sheath, with the result that under the application of a circumferential force such as applied by the inflation of a catheter balloon, the seam is disrupted thereby freeing the stent for deployment as by self-expansion or further balloon expansion.

Figure 9:
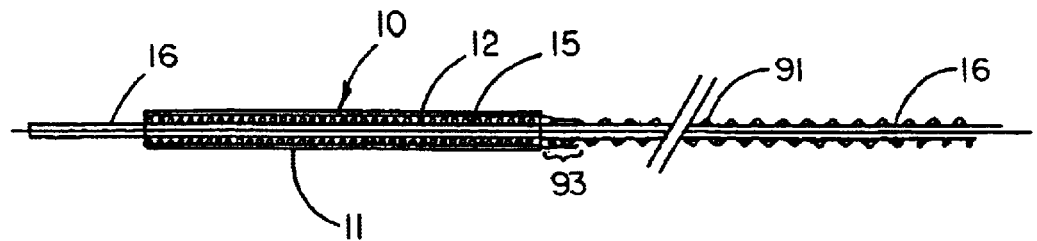
FIGS. 9, 9A and 9B are longitudinal cross sections of an alternative embodiment wherein the constraining sheath is partially everted over the endoprosthesis and may use an optional spring component to aid in endoprosthesis deployment by full eversion of the constraining sheath.
Figure 9A:
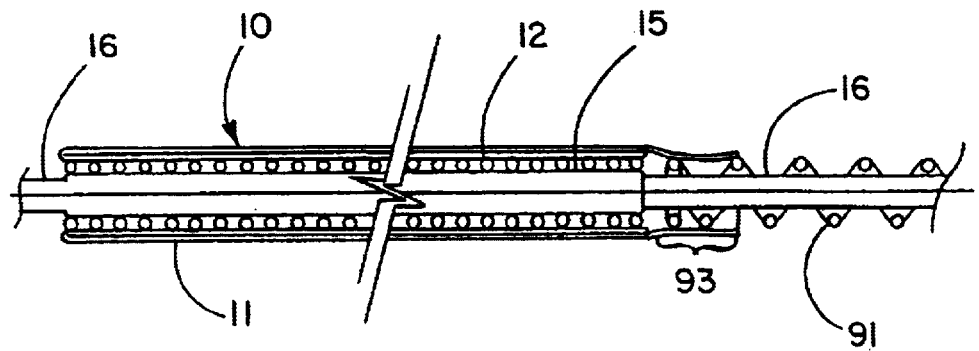
Figure 9B:
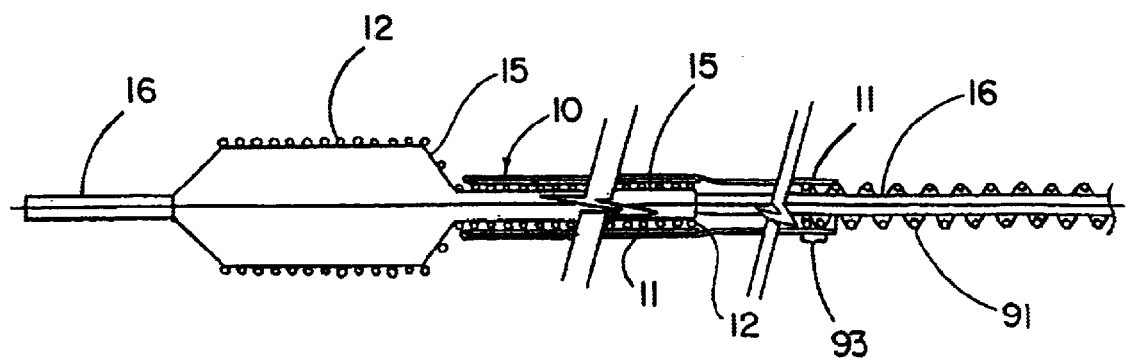

FIGS. 9, 9A and 9B are longitudinal cross sections that relate an alternative embodiment wherein the constraining sheath 11 is in the form of an everted tubular component that extends from the hub end to the tip end of the endoprosthesis. Constraining sheath 11 then extends back over itself to reach back to the hub end and beyond to an attachment region 93 wherein the hub end of sheath 11 is joined to another component such as a catheter shaft of either elastic or non-elastic material, or alternatively to a spring component. While the close-up view of FIG. 9A describes a coil spring component 91 to which the hub end of the everted constraining sheath 11 is attached, it can be replaced if desired with tubing or a fiber of either elastic material such as silicone or relatively inelastic material such as polyethylene. FIG. 9A shows this embodiment as it would appear prior to deployment. Spring component 91 is attached to the constraining sheath 11 under tension, but with the spring tension low enough that the sheath 11 is not caused to come free of the endoprosthesis 12 during insertion into a body conduit 20 (not shown here). FIG. 9B describes the system partially deployed, with the everted constraining sheath still further everted as it is withdrawn toward the catheter hub. Inflation of balloon 15, aided by the tension in spring 91, results in release and deployment of the endoprosthesis from within the sheath 11 as the sheath is further everted. Following full eversion of the sheath 11 and full release and deployment of the endoprosthesis 12, the sheath is removed from within the body conduit 20 along with the catheter 16.

Figure 10A:
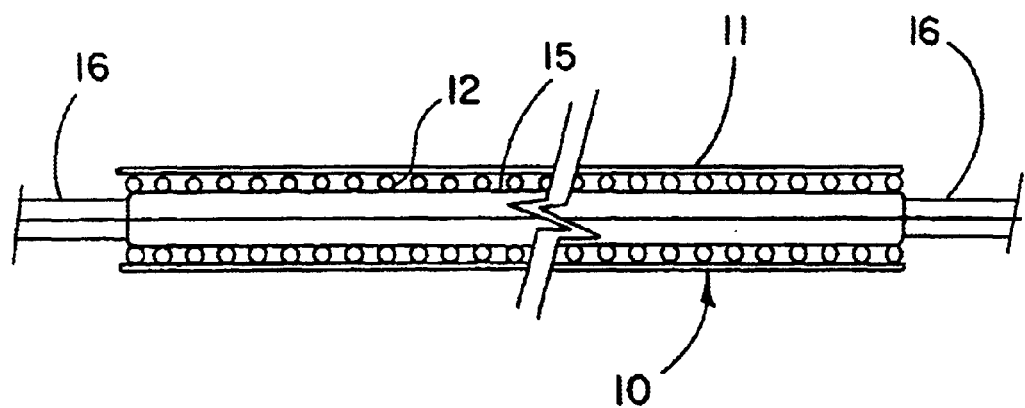
FIGS. 10A and 10B are longitudinal cross sectional views of an alternative embodiment wherein inflation of a catheter balloon pushes the constraining sheath off of the endoprosthesis in the direction of the catheter hub.
Figure 10B:
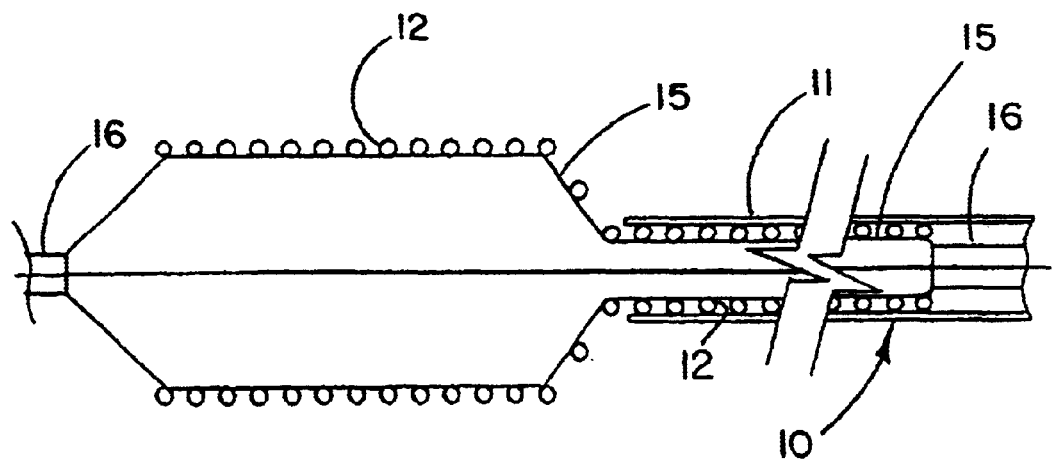
Figure 11A:
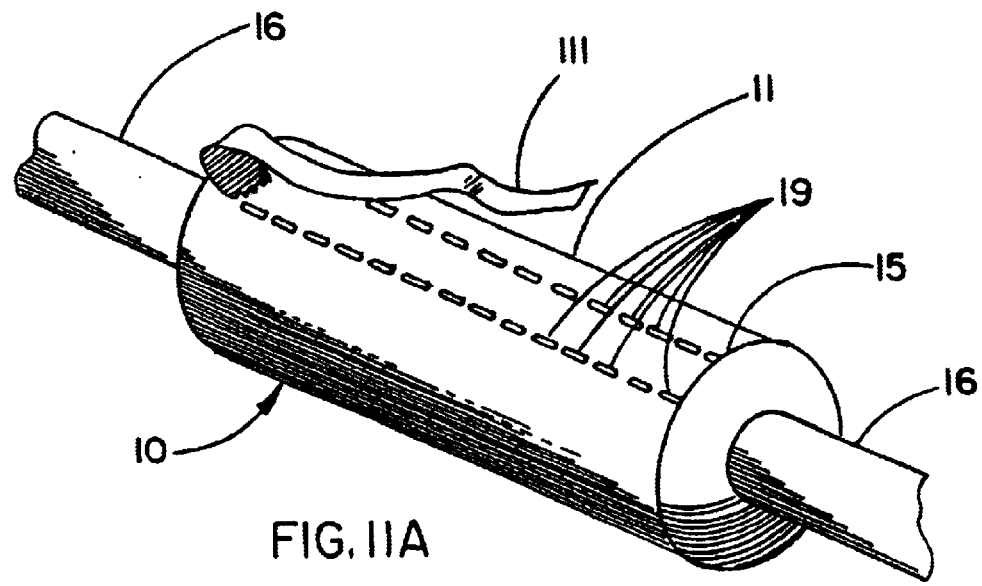
FIGS. 11A and 11B are perspective views of a constraining sheath that releases a contained endoprosthesis by a pull string release incorporated into the constraining sheath.
Figure 11B:
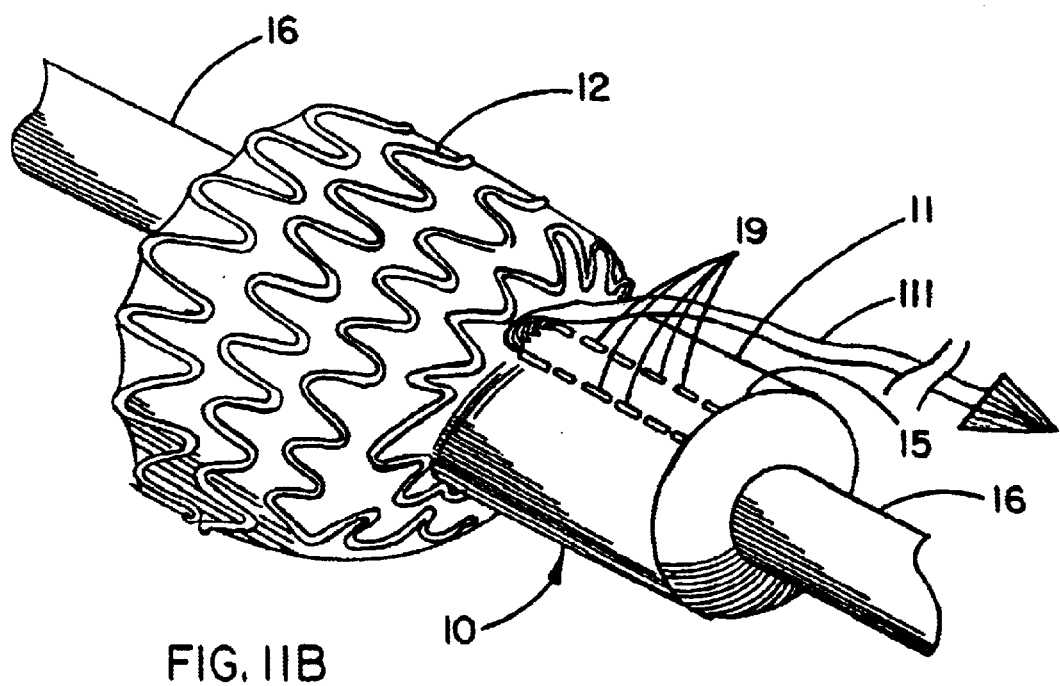

FIGS. 10A and 10B describe longitudinal cross sections of still another embodiment wherein the constraining sheath is pushed free of the endoprosthesis by initial inflation of the catheter balloon. FIG. 10A shows the system prior to deployment while FIG. 10B shows the endoprosthesis partially deployed. The system shown by FIG. 10A uses an endoprosthesis that yields to the expanding force of the catheter balloon at the tip end first. The lubricious sheath resists this change in diameter and is pushed in the direction of the catheter hub as indicated by FIG. 10B. Continued inflation of the catheter balloon continues to move the constraining sheath toward the hub end of the catheter. Preferably, the hub end of the constraining sheath is attached to a catheter shaft, which enables the constraining sheath to be fully withdrawn following complete release of the endoprosthesis. Alternatively, elastic or inelastic components can be used for attachment to the catheter and/or to facilitate withdrawal FIGS. 11A and 11B are perspective views of a constraining sheath 11 provided with a pull string release 111. As shown by FIG. 11A which describes the system prior to deployment, the constraining sheath 11 is provided with two adjacent parallel rows of perforations 19 and a pull string 111 affixed to, or integral with, the distal or tip end of the portion of the constraining sheath 11 located between the adjacent parallel rows of perforations 19. The pull string 111 is extended along the catheter shaft 16 to the hub to allow for tension to be applied when the endoprosthesis 12 is located as desired and ready for deployment. FIG. 11B shows the endoprosthesis 12 partially deployed, wherein the application of tension to the pull string release 111 results in the peeling back of the portion of constraining sheath material located between the adjacent parallel rows of perforations 19, with the result that the sheath is disrupted beginning from the tip end and progressing to the hub end, simultaneously freeing the self-expanding endoprosthesis 12 for deployment against the luminal wall of the body conduit within which it has been placed.

Figure 12A:
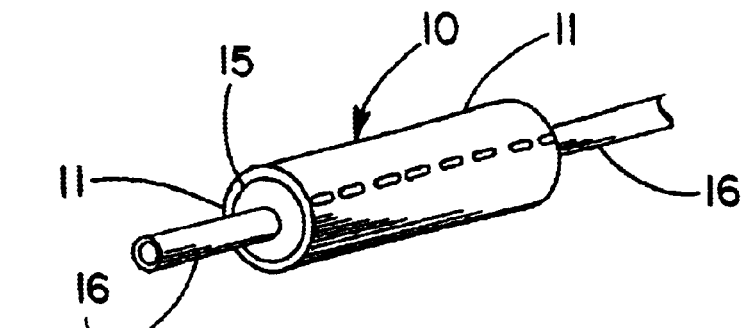
FIGS. 12A–12C describe a constraining sheath provided with a fully circumferential distensible cover.
Figure 12B:
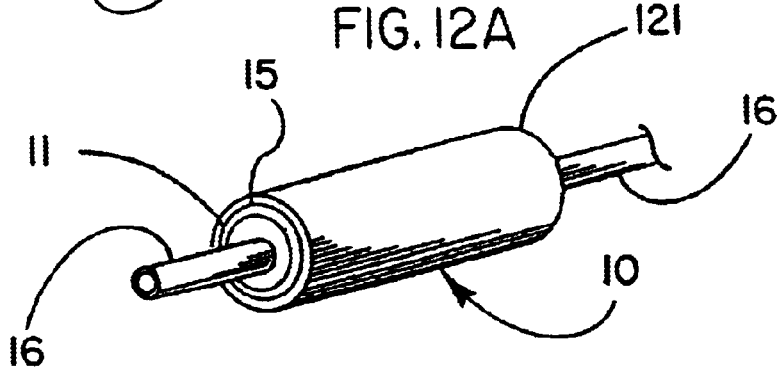
Figure 12C:
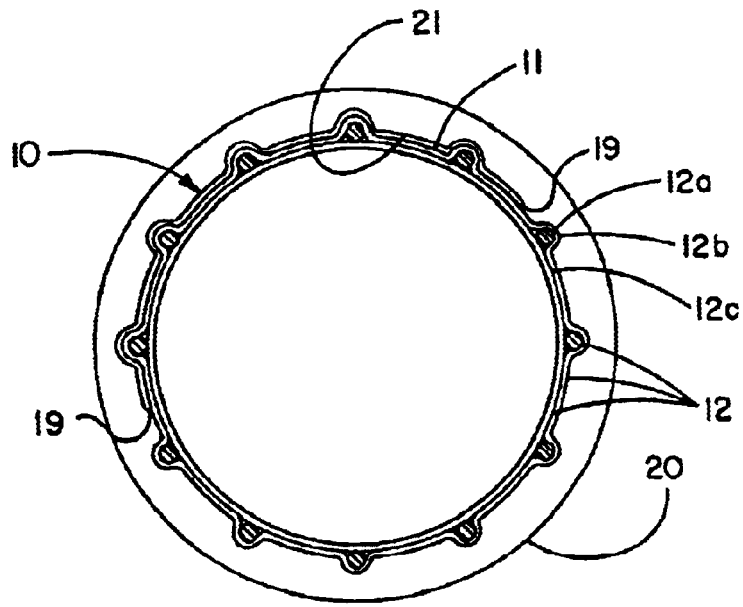

FIGS. 12A and 12B describe perspective views of an alternative embodiment wherein the constraining sheath assembly 10 of the present invention shown in FIG. 12A is provided with a fully circumferential distensible cover 121 as shown by FIG. 12B. When deployed by disruption of the underlying constraining sheath, such a cover will distend to the final diameter of the deployed device. The fully circumferential cover 121 can be used to reduce the rate at which deployment occurs and/or to serve as a cover over the stent in the fashion of a stent graft. The transverse cross section of FIG. 12C shows a device of this type as deployed in a living vessel, wherein the fully circumferential cover 121 when fully deployed functions as the outer stent cover 12b shown previously in FIG. 3B. This distensible cover can be placed either external to the constraining sheath 11 as shown, or alternatively may be placed internally to constraining sheath 11.

Distensible tubular covers of this type are known; a preferred cover is a thin (e.g., 0.5 mm), longitudinally extruded and expanded ePTFE tube. An alternative ePTFE distensible tube is described by published PCT Patent Application WO97/02791.

Figure 13A:
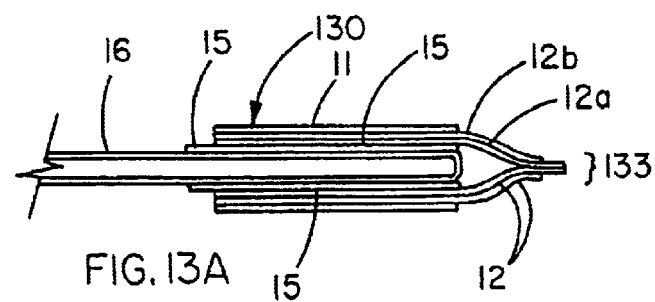
FIGS. 13A–13D are side views of an occluder and a filter device in the form of an endoprosthesis having a closed end which may be practically deployed with the constraining sheath of the present invention.

The various embodiments of the constraining sheath of the present invention can also be used with occlusion devices that are in the form of covered stents having at least one end closed so as to partially or completely block the passageway into which it is inserted. Such an occlusion device 130 is shown by the side view of FIG. 13A in compacted form ready for insertion into the vasculature. Stent component 12a is provided with covering 12b, which are joined at location 133 beyond the tip end of the catheter shaft 16. Constraining sheath 11 secures the self-expanding endoprosthesis 12 around deflated catheter balloon 15.

Figure 13B:
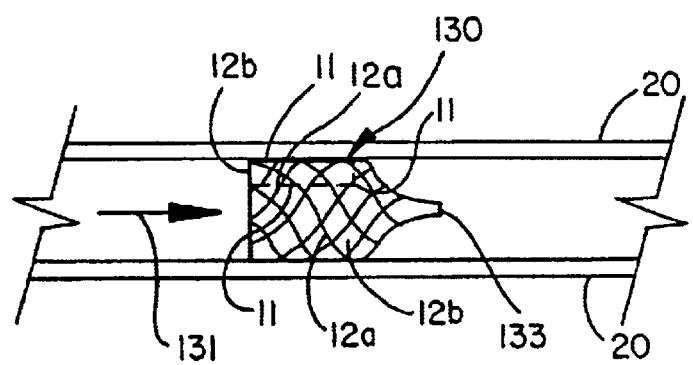

The occluder is shown in FIG. 13B deployed within a body conduit 20, with the direction of normal flow within the body conduit 20 indicated by arrow 131. The constraining sheath 11 has been disrupted and is left captured between stent covering 12b and the lumen of body conduit 20. Alternatively, if the constraining sheath has been provided secured to the catheter shaft 16, it may be removed along with the catheter shaft 16 following deployment of the occlusion device 130. The covering 12b over stent component 12a provides occlusion of the body conduit 20.

Figure 13C:
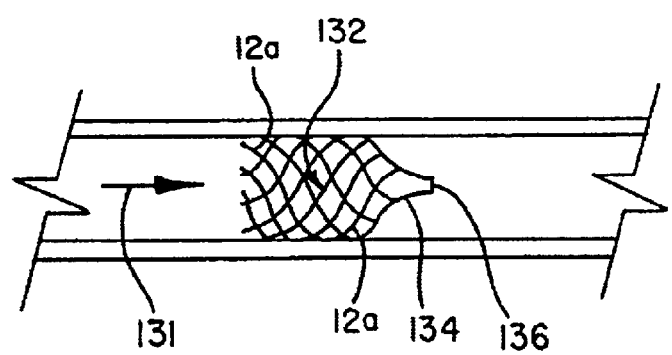

As shown by FIG. 13C, this embodiment can be used with stent component 12a to create a permanent or temporary filter 132 for a body conduit 20, such as, for example, a vena cava filter. Again, the constraining sheath 11 can be left between the stent component 12a and the luminal surface of the body conduit 20, or as represented by FIG. 13C, constraining sheath 11 can be withdrawn entirely along with the catheter shaft 16 following deployment. The tip end 134 of the device remains substantially closed, having only a small tip opening 136 of size similar to the other openings through the filter provided by the interstices through the stent component 12a.

Figure 13D:
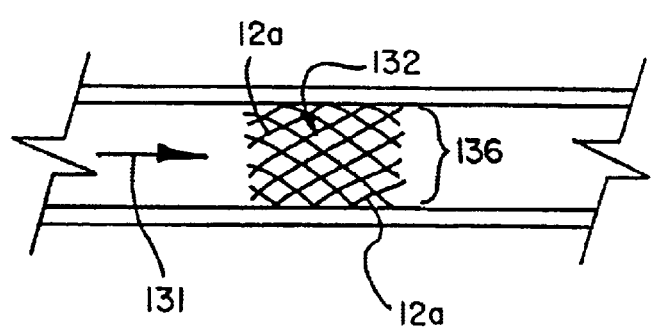

When filtering is no longer needed, a catheter balloon can be inserted into small tip opening 136 and inflated to open the filter 132 up entirely. As shown by FIG. 13D, this leaves the stent component 12a in full contact with the luminal surface of the body conduit 20, thereby restoring full flow to the body conduit without any filtering.

Figure 14A:
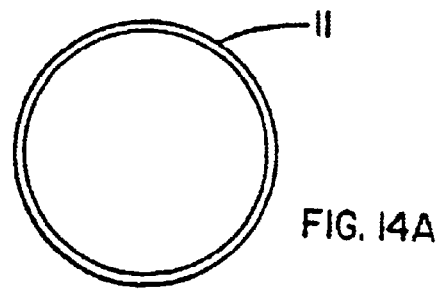
FIGS. 14A–14G describe transverse cross sections of an alternative embodiment of the constraining sheath wherein the tubular sheath is folded around a compacted endoprosthesis and a deflated catheter balloon at their small, insertion diameters, with the folded sheath material temporarily bonded at selected points, wherein the bonds shear apart during inflation of the catheter balloon.
Figure 14B:
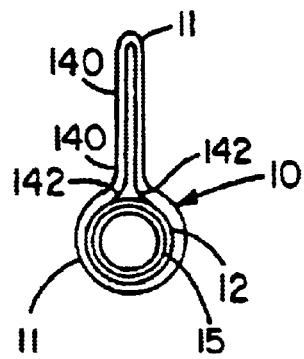
Figure 14C:
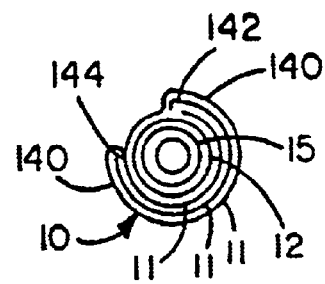

FIGS. 14A–14G show transverse cross sections of an alternative constraining sheath wherein the sheath component is provided at the full size, indicated in FIG. 14A, at which it is intended to be deployed. FIG. 14B describes the assembly of this embodiment wherein the constraining sheath 11 is fitted around the compacted endoprosthesis 12 and catheter balloon 15 (i.e., the stent and balloon are at their compacted diameter at which they will be inserted into the vasculature). The excess material of the constraining sheath 11 results in flap 140. This flap 140 is preferably bonded together temporarily along adjoining inner surfaces 142. The bonding of these inner surfaces 142 allows the constraining sheath to hold the compacted endoprosthesis and deflated balloon at their small, compacted diameters for insertion into the vasculature. The bonding may be accomplished with a biocompatible adhesive such as a medical grade silicone or may alternatively be done by thermally bonding the opposing inner surfaces 142. It is most preferred that the area of bonded surfaces be minimal in order to allow them to separate easily during subsequent inflation of the catheter balloon 15 for deployment of the endoprosthesis 12. The final assembly step is shown in FIG. 14C wherein flap 140 is wrapped around the outer surface of the device 10. Preferably, the end of flap 140 is temporarily secured at location 144 by bonding as performed previously at location 142.

In use, the embodiment of FIG. 14C is inserted into the vasculature to a desired location. When located as desired within the vasculature, the device 10 is deployed by inflation of catheter balloon 15, resulting in disruption of the bonded regions 142 and 144. The shearing of these bonds then allows the constrained endoprosthesis 12 to deploy to its full diameter. The constraining sheath remains located between the wall of the blood vessel and the fully deployed endoprosthesis 12. Alternatively, as described previously for other embodiments, if the constraining sheath has been provided with its hub end secured to the shaft of the balloon catheter adjacent to the balloon, the constraining sheath 11 may be removed along with the balloon catheter.

Figure 14D:
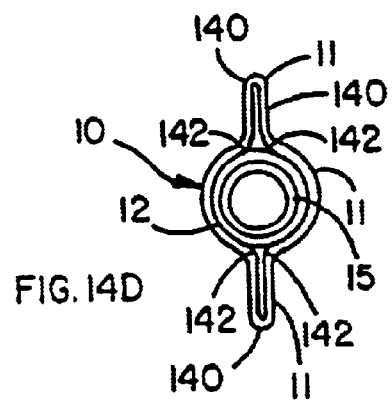
Figure 14E:
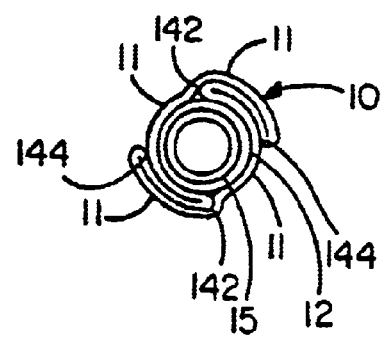

Another method of folding the excess flap material 140 is described by FIGS. 14D and 14E. In this embodiment, two opposing flaps are created per FIG. 14D and temporarily bonded at points 142. The two flaps are then wrapped around the exterior of the device 10 and preferably secured at locations 144. Again, deployment is accomplished by inflation of the catheter balloon 15, shearing the bonds at locations 142 and 144 and allowing the endoprosthesis 12 to deploy to its full diameter.

Figure 14F:
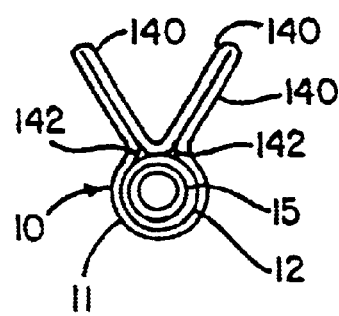
Figure 14G:
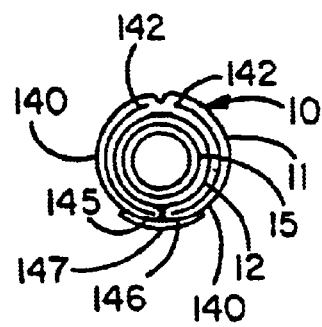

Alternatively, as shown by FIG. 14F, a pair of adjacent flaps 140 may be created and folded down around endoprosthesis 12 in opposing directions per FIG. 14G. These flaps may be secured by permanently bonding a strip 147 of biocompatible material to the end of one of the flaps at location 145 and temporarily bonding it at location 146. Upon deployment initiated by inflation of balloon 15, the strip remains secured to the exterior of the constraining sheath 11 at location 145.

It is apparent from FIGS. 14A–14G that a variety of folded and temporarily bonded embodiments of the constraining sheath 11 are possible, including embodiments where a fold is placed inside the portion of the constraining sheath material that wraps around the compacted endoprosthesis.

Figure 15A:
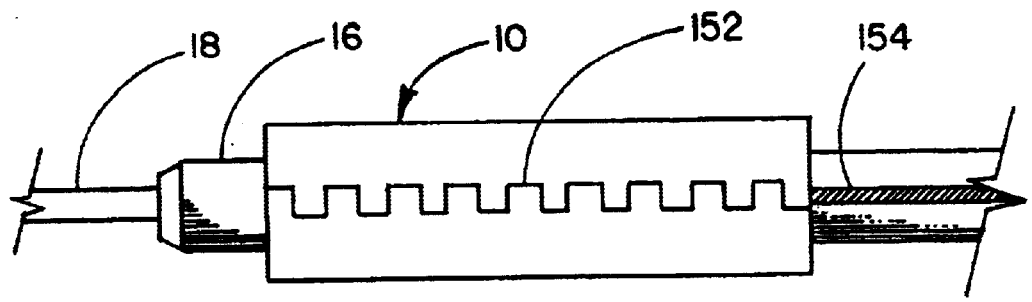
FIGS. 15A–15C describe constraining sheath having a hinge line as the means for disruption.
Figure 15B:
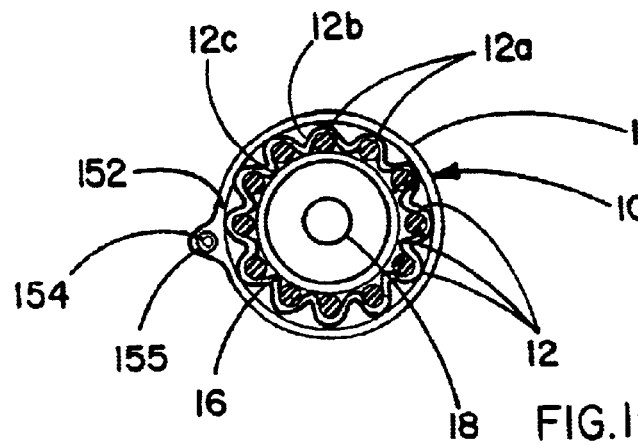
Figure 15C:
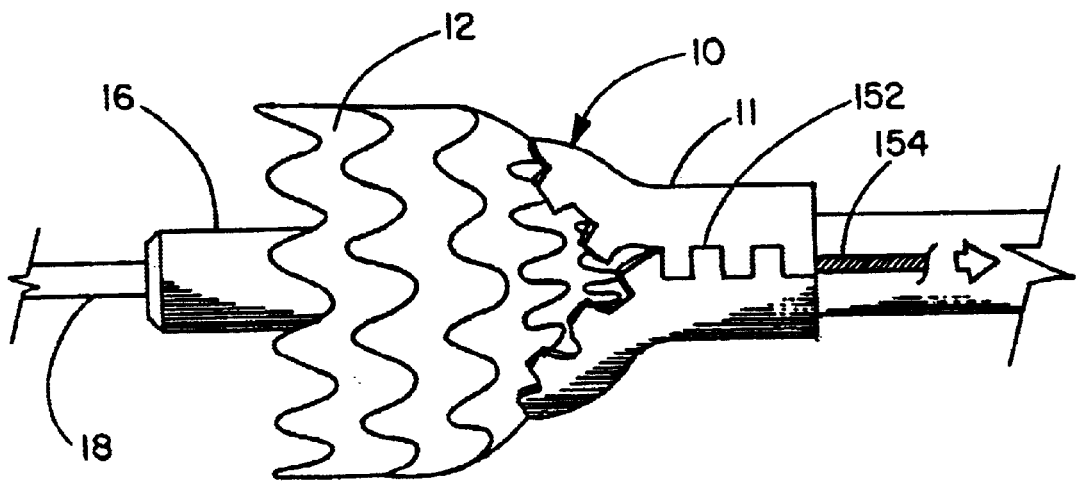

FIGS. 15A–15C describe an alternative embodiment wherein the constraining sheath 11 is provided with a seam in the form of a hinge 152. The constraining sheath 11 is an ePTFE tube preferably made by helically wrapping an ePTFE film around the surface of a mandrel of diameter corresponding to the desired inside diameter the constraining sheath 11. A preferred ePTFE film is a composite of ePTFE and fluorinated ethylene propylene (FEP) wherein the FEP is applied to the ePTFE film as a discontinuous coating that allows the film to remain porous. These composite films are made as taught by U.S. Pat. No. 5,358,516 to Myers et al.

The hinge 152 is created by placing a small tube 155 (seen in the transverse cross section of FIG. 15B) of longitudinally extruded and expanded ePTFE, having inside and outside diameters of, for example, 0.25 mm and 0.30 mm, on the outer surface of the constraining sheath tube 11 parallel to the longitudinal axis of the sheath tube 11. A metal wire of diameter the same as or slightly smaller than the inside diameter of the small ePTFE tube 155 is inserted into the lumen of the small ePTFE tube 155 for its full length. An additional layer of ePTFE film is wrapped over the outer surface of the sheath tube 11 to secure the small ePTFE tube 155 to the outer surface of the constraining sheath 11. The resulting construct is then placed into an oven set at 320 degrees C. for a time of about 5 minutes, in order to thermally bond the PTFE/FEP components together. After being allowed to cool, a laser is used to cut the desired hinge pattern 152 through the wall thickness of the constraining sheath tube 11, except for material immediately under the metal wire and therefore shielded from the laser by the wire. This small amount of uncut material will subsequently yield when the constrained endoprosthesis 12 is released for deployment, as will be described.

Following cutting of the desired hinge pattern 152 with the laser, a length of strand material 154 such as ePTFE suture is attached to an exposed end of the wire protruding from an end of the small ePTFE hinge tube 155. The strand material 154 is of the same or smaller diameter than the wire, and is of length greater than the length of the catheter shaft 16 that will be used with the resulting endoprosthesis assembly 10. The attachment of the strand 154 to the wire is preferably done as an end-to-end square-cut butt joint of the two parts using an adhesive such as a cyanoacrylate in order that the diameter is not increased at the point of attachment. The wire is then pulled from the opposite end of the constraining sheath 11, thereby pulling the strand 154 into the lumen of the small ePTFE tube 155. Once the strand 154 extends through the full length of the small ePTFE tube 155 now serving as the hinge tube, the strand 154 is cut adjacent to the point of attachment with the wire, and the wire is discarded. An endoprosthesis 12 at its small, compacted diameter may now be inserted into the completed constraining sheath 11.

Alternatively to ePTFE strand 154, the wire used in the manufacture of the hinged constraining sheath 11 may be provided with adequate length to allow its use as the strand 154 that disrupts the sheath 11 to initiate deployment of endoprosthesis 12.

FIG. 15A describes a side view of this embodiment of the endoprosthesis assembly 10 and constraining sheath 11, while FIG. 15B shows a transverse cross section of the endoprosthesis assembly 10. In use, as described by the side view of FIG. 15C, the self-expanding endoprosthesis 12 is released for deployment by applying tension to the strand 154, causing the strand 154 to move toward the hub end of the assembly 10 thereby allowing the two sides of the hinge 152 to separate and disrupt the constraining sheath 11.

Figure 16A:
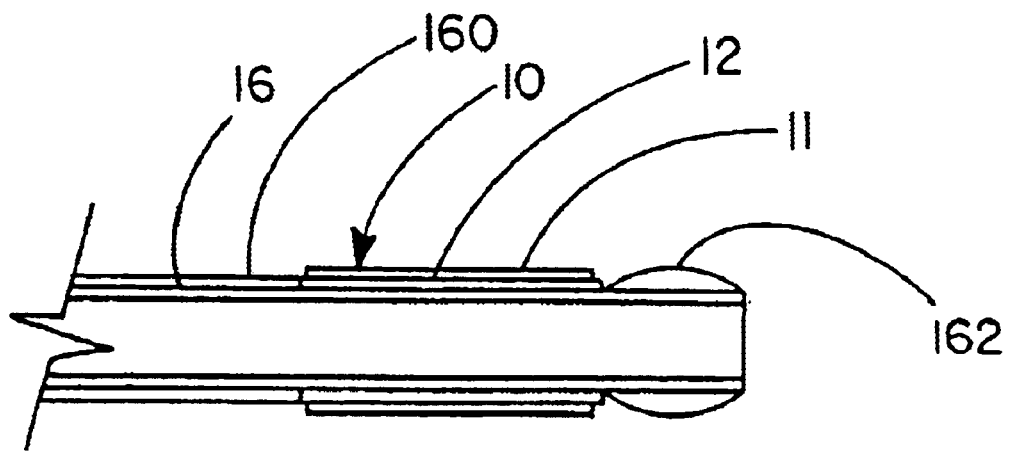
FIGS. 16A and 16B describe an "olive" movable through the endoprosthesis assembly as an alternative method of initiating the means for disruption.
Figure 16B:
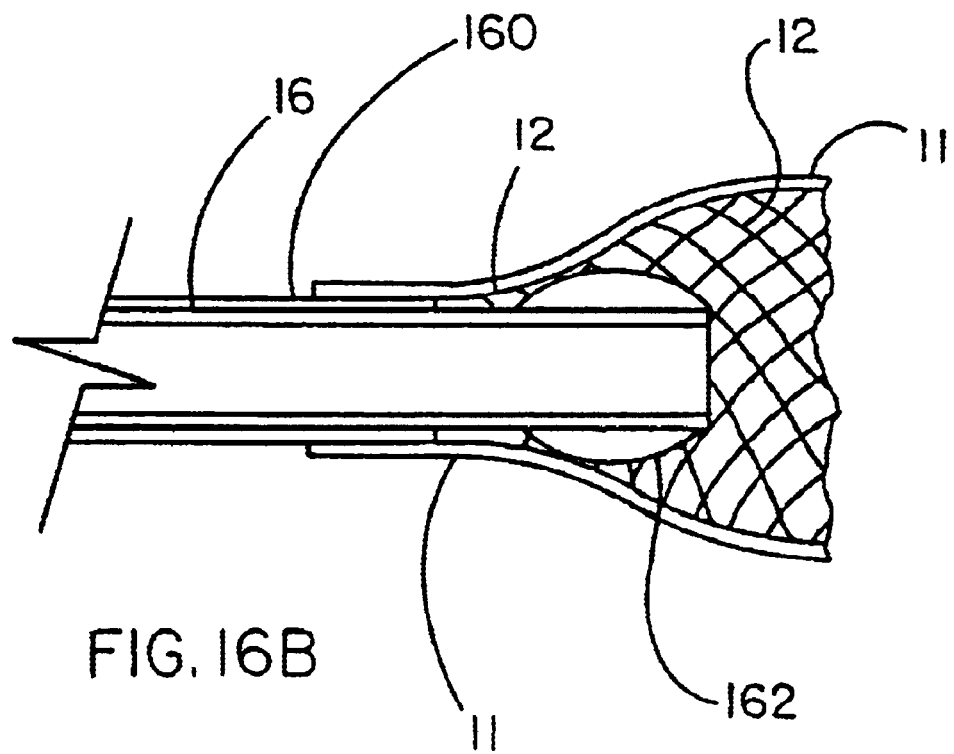

The means for disruption, in the form of perforations, a seamline or various other means, can be initiated by inflation of a catheter balloon as described above. The balloon's inflated diameter should be of a size sufficient to disrupt the perforations. The balloon's inflated diameter can be varied along the length such that all diameters are large enough to create constant disruption, but some locations are small enough to not oppose the wall of the fully deployed self-expanding endoprosthesis. Other initiating methods are possible, including the pull string system described in FIGS. 11A–11B. Another initiating method involves the use of an object of larger diameter than the inside diameter of the endoprosthesis in its compacted, small diameter state. As shown by the longitudinal cross section of FIG. 16A, such an object or "olive" 162, can be attached to a guidewire or catheter shaft 16 extending through the endoprosthesis 12 and constraining sheath 11, with the "olive" 162 located at the tip end of the endoprosthesis assembly 10. Outer catheter shaft 160 is provided coaxially around but not attached to catheter shaft 16, serving as a stop against the hub end of endoprosthesis 12. Tension applied to the guidewire or catheter shaft 16 (pulled against outer catheter shaft 160) results in the olive 162 being pulled through the endoprosthesis 12 and constraining sheath 11. As shown by the cross section of FIG. 16B, the movement of the olive 162 through the endoprosthesis assembly 10 provides a distending force to the constraining sheath 11, thereby initiating the means for disruption, be that perforations, a seamline or other means. Disruption of the constraining sheath 11 results in expansion and deployment of the self-expanding endoprosthesis.

The constraining sheath can be made from various materials which are adequately biocompatible to be permanently implantable. ePTFE has been described as a preferred material. Other suitable materials may include non-porous PTFE, polypropylene and polyethylene terephthalate. Other less biocompatible materials may be used if the sheath is configured to be removed along with the catheter such as by the embodiment described by FIGS. 6A and 6B.

Figure 17:
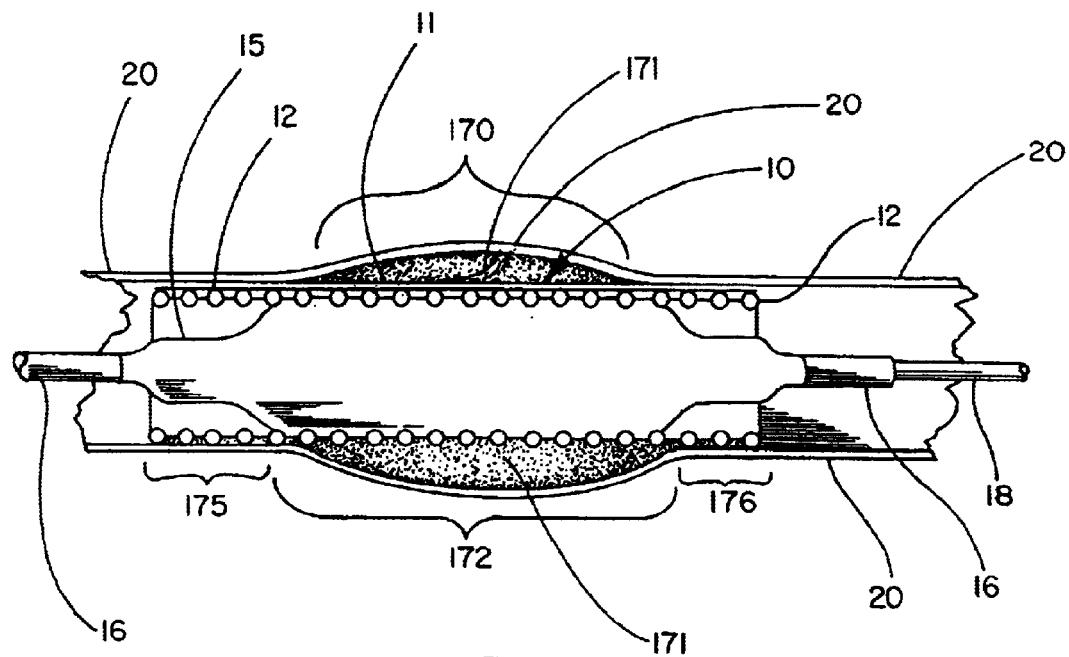
FIG. 17 shows a fully deployed endoprosthesis within a vessel, that utilizes a deployment balloon with a working length substantially shorter than that of the endoprosthesis.

FIG. 17 shows a longitudinal cross section of a further embodiment of the invention, with self-expanding endoprosthesis 12 deployed within vessel 20. The deployed endoprosthesis 12 underlies and extends beyond the treated region 170 within the vessel 20. This region 170 may initially consist of, for example, a stenotic plaque 171. To deploy this endoprosthesis 12, a balloon 15 mounted on the distal end of a delivery catheter 16 has been inflated to disrupt or burst an overlying constraint 11. After deployment of the endoprosthesis 12, the disrupted constraint 11 is located between the deployed endoprosthesis 12 and the vessel wall 20. The balloon 15 is composed of three regions: a proximal region 174, a middle region 172 and a distal region 176. The proximal 174, middle 172 and distal 176 regions all inflate to a diameter large enough to disrupt constraint 11. However, the end balloon segments 174, 176 will not contact the endoprosthesis 12 when the endoprosthesis 12 is fully deployed and the proximal 174 and distal 176 balloon segments are fully inflated. Therefore, the working length of the balloon 15, defined as the middle region 172 that is in contact with a portion of the length of the lumen of the endoprosthesis when deployed within vessel 20, is less likely to cause circumferential stretching of the vessel outside of the treated region 170 (i.e., outside of middle balloon region 172). Less trauma to the vessel surrounding the proximal 174 and distal 176 regions of the balloon is believed to create less of an inflammatory response at the ends of the endoprosthesis 12. The working length of the balloon is preferably less than about 90 percent of the length of the endoprosthesis. If the ends of the endoprosthesis are not uniformly even, then the length of the endoprosthesis is taken to be its maximum length measured from points on the ends that extend furthest from the middle of the length of the endoprosthesis. The working length of the balloon can be less than about 90 percent, less than about 80 percent of the length of the endoprosthesis, or less than about 70 percent of the length of the endoprosthesis, or less than about 60 percent of the length of the endoprosthesis, or less than about 50 percent of the length of the endoprosthesis. These shorter balloon working lengths are in contrast to the typical balloon that is of equal or greater length than the endoprosthesis that it is used with.

The following example is intended to describe one method of making the constraining sheath. The invention is not limited to the method described therein and it will be apparent that various methods and materials might be effectively used. For example, a simple ePTFE tube made from longitudinally extruded and expanded PTFE, and subsequently provided with a means for controlled disruption such as a row of perforations, may be employed as the constraining tube.

EXAMPLE 1

A 0.7 mm inside diameter ePTFE tube of about 20 cm length, about 0.03 mm thick and about 30 micron fibril length is fitted over a stainless steel mandrel of about 1.4 mm diameter. This tube is intended as a sacrificial tube upon which the constraining sheath is subsequently constructed. One end of the ePTFE tube is helically wrapped for a length of about 1 cm with another length of the same ePTFE tubing; this wrap is also sacrificial and intended only to later enable the release of the subsequently applied constraint sheath material. As such, both the underlying ePTFE tube fitted over the mandrel and the helically wrapped material are non-critical choices as long as they are capable of tolerating subsequent heat processing without becoming adhered to the constructed constraint sheath.

Next, four layers of ePTFE/FEP porous film laminate are applied from a roll of this film over the sacrificial ePTFE tube and helical wrap. The ePTFE film used to manufacture this laminate is of a type made as taught by U.S. Pat. No. 5,814,405 to Branca, et al. The laminated film used is of about 0.02 mm thickness and has an estimated mean fibril length of about 100 microns. The mean fibril length is estimated by examining scanning electron photomicrographs of the film surface. A length of about 18 cm is covered by the wrap, leaving about one centimeter of the underlying sacrificial ePTFE tube extending beyond each end of the wrap. The film is oriented with the direction of the fibrillar microstructure perpendicular to the longitudinal axis of the mandrel; the FEP coated side of the film faces away from the mandrel surface. A characteristic of the ePTFE film laminate chosen for the application (but atypical for ePTFE films generally) is that it splits cleanly in a direction perpendicular to the fibrils, i.e., parallel to the nodes when a suitable force is applied. It is anticipated that any ePTFE film would be suitable as long as it is able to be split in a direction parallel to the longitudinal axis of the resulting constraining sheath.

A gold metal strip of about 0.05 mm thickness and 0.37 mm width is placed onto the surface of the film with the length of the gold strip parallel to the longitudinal axis of the mandrel, after which a fifth layer of the film is wrapped around the mandrel, thus covering the gold strip with one layer of the film. The gold strip is intended to serve as a radiopaque marker band during use. It is apparent that other such markers might also be used.

The edge of the film is then tacked down, using a heated iron, to the underlying layers of film and the underlying ePTFE sacrificial tube using a temperature adequate to melt the FEP. The assembly is placed into an air convection oven set at a temperature of about 320° C. for a time of about 5 minutes, after which it is removed and allowed to cool.

On the side of the film tube directly opposite the gold marker ribbon (180 degrees of revolution away), the film tube is perforated using a cutting mechanism, such as a laser. Perforations of rectangular shape are provided along the entire length of the film tube, with each perforation being of about 0.5 mm length and 0.25 width, spaced apart by a distance of about 0.5 mm.

One additional wrap of the same film is applied in the same fashion as the previous layers, except that this layer covered about 17 cm of the length of the previously wrapped length while leaving one end of about 1 cm length not covered with this additional layer. The 1 cm length not covered by this layer is intended to be located at the distal or "tip" end of the completed endoprosthesis assembly and, being thinner, will enable disruption of the sheath during the initial balloon inflation to begin at the tip end of the assembly. It is apparent that this and other methods may be used to cause disruption to initiate at a desired location.

Following this step, the entire 18 cm wrapped length is provided with two additional wraps. The entire assembly is again heated in a convection oven and cooled as was done previously. The mandrel is then removed from the assembly, after which the sacrificial helical wrap is removed to create a release plane between the construct and sacrificial liner. This enables the subsequent removal of the film tube from the underlying sacrificial ePTFE tube by everting of the film tube, beginning at the end from which the helical wrap has been removed, back over the underlying ePTFE tube while the free end of the sacrificial ePTFE tube is simultaneously pulled from the everting film tube. The everted film tube thus has the FEP side of the film facing inward with the perforations on the outer surface.

While this example describes the constraining sheath made to specific dimensions, it is apparent that similar construction methods may be used with a variety of dimensions. Likewise, wide variations in the construction method may be used to create a predictably disruptable constraining sheath.

The constraining sheath is trimmed transversely, flush with the first perforation on the end that has one less layer of film. A 4 mm×40 mm self-expanding stent graft in the form of a nitinol stent provided with both inner and outer coverings of ePTFE is drawn through a tapered die in order to collapse it in diameter to a minimum diameter for insertion into a vasculature, and captured within the above-described constraining sheath. During capture, the end of the stent graft is aligned flush with the end of the constraining sheath.

The opposite end of the constraining sheath is then carefully trimmed flush with the opposite end of the stent graft. The constraining sheath is attached to the stent graft by applying a local heat source to the constraining sheath at a location 180° from the perforations. The heat source caused the FEP on the inside of the constraining sheath to flow and adhere to the ePTFE outer covering of the stent graft residing within it. This assembly is then loaded onto a 4 mm×40 mm angioplasty balloon. The stent graft is carefully aligned with the radiopaque markers on the balloon catheter shaft.

The balloon is inflated in a water bath heated to about 37° C. to approximate human physiology. The constraining sheath ruptures in the prescribed manner (from the tip of the catheter toward its hub) and at a prescribed balloon pressure of about 6 atmospheres. Following deployment, the constraining sheath remains attached to the stent graft.

The present invention involves the application of a thin, disruptable constraint as the restraining mechanism for delivery of a self-expanding stent. Deployment of the self-expanding stent is affected by balloon dilatation and concurrent constraint disruption. Due to the clinical requirements that this delivery system (1) achieve low balloon pressure (e.g., about 6 atmospheres) delivery thereby avoiding adjacent vessel trauma, (2) maintain low delivery and crossing profiles, and (3) exhibit high flexibility, it is advantageous for the constraining sheath be as thin and delicate as possible. Inherent in the mechanical properties of a thin and delicate material is the tendency to yield under an applied load. A further embodiment of the present invention relates to such a yielding, delicate constraining sheath designed to specifically address the clinical needs. Additionally, the present invention relates to the application of a secondary restraining device that can be used in packaging to prevent yielding of the constraint beyond the desired delivery and crossing profiles. This secondary restraining device, or packaging sheath, is intended to be removed before the device is introduced into the body. While this inherently requires an additional step in the device preparation procedure, it is quickly performed without adding any appreciable time to the procedure.

In summary, this further embodiment of the present invention relates to a constraining sheath whose inherent yield characteristics have been exploited to achieve low delivery and crossing profiles, high flexibility during delivery and low deployment balloon pressures.

The packaging sheath is designed to prevent unwanted growth of the deployment system and indwelling endoprothesis throughout its packaging process, sterilization process and intended shelf life. Because the packaging sheath is removed immediately prior to insertion into the body and is not intended for implantation, it may be constructed using very high strength materials (whether biocompatible or otherwise), employ very thick wall cross sections, use multiple layers or any combination thereof.

Figure 18:
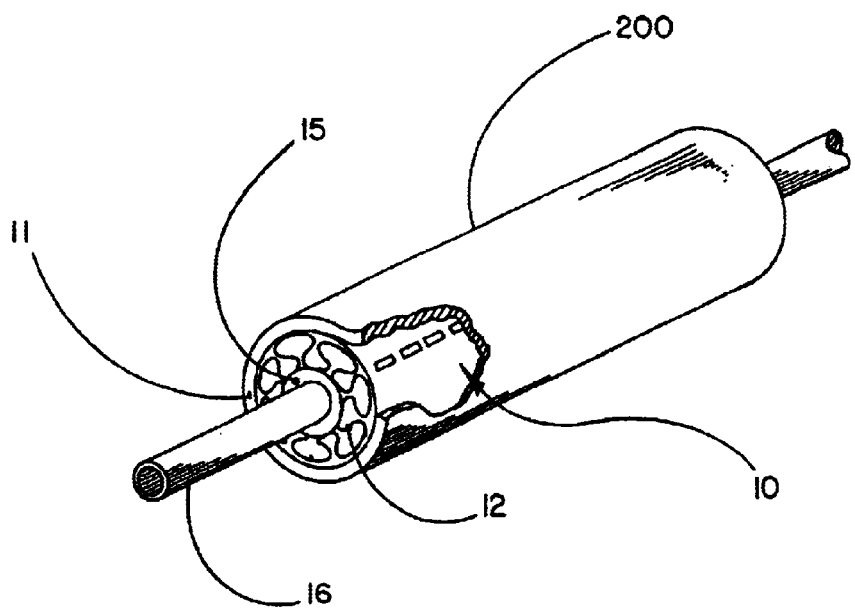
FIG. 18 is a perspective view of the packaging sheath containing the present invention.

FIG. 18 depicts a perspective view of a packaging sheath 200 that at least partially contains the constraining sheath assembly 10 of the present invention, therefore providing a protective packaging device as well as providing protection from unwanted diametrical growth of the constraining sheath assembly 10 (i.e., the endoprosthesis assembly of the present invention). When it is said that the packaging sheath "contains" the constraining sheath assembly 10, it is meant that the packaging sheath 200 provides a circumferentially oriented constraint about at least a portion of the length and/or circumference of the assembly 10 such that a further increase in the circumference of the contained sheath assembly is prevented while the packaging sheath 200 is in place.

Figure 19:
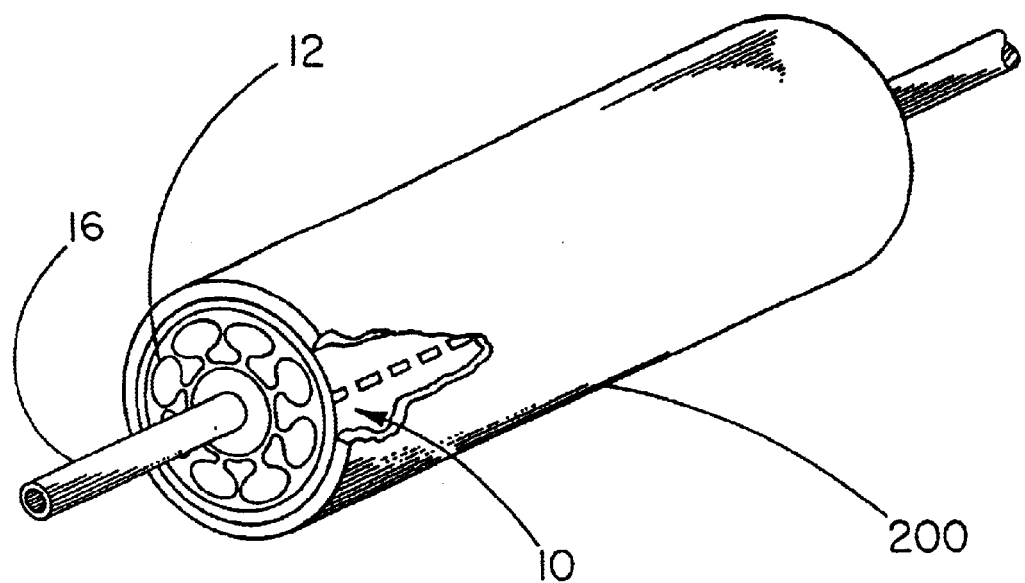
FIG. 19 is a perspective view depicting the packaging sheath configured as a single, continuous tube containing the present invention.

FIG. 19 is a perspective view of the packaging sheath 200 wherein the packaging sheath comprises a tube fully containing the constraining sheath assembly 10 including indwelling endoprothesis 12. In this configuration, the packaging sheath 200 may be made of a strong polymeric or metallic material and is preferably made of a transparent, lubricious, inert polymer. Possible materials for the packaging sheath would include, for example, polycarbonate, polyethylene, PTFE, FEP, polyurethanes, carbon, glass, nylon, silk, various metals. The packaging sheath 200 is removed by sliding it axially away from the sheath assembly until it completely exposes constraining sheath assembly 10.

Figure 20:
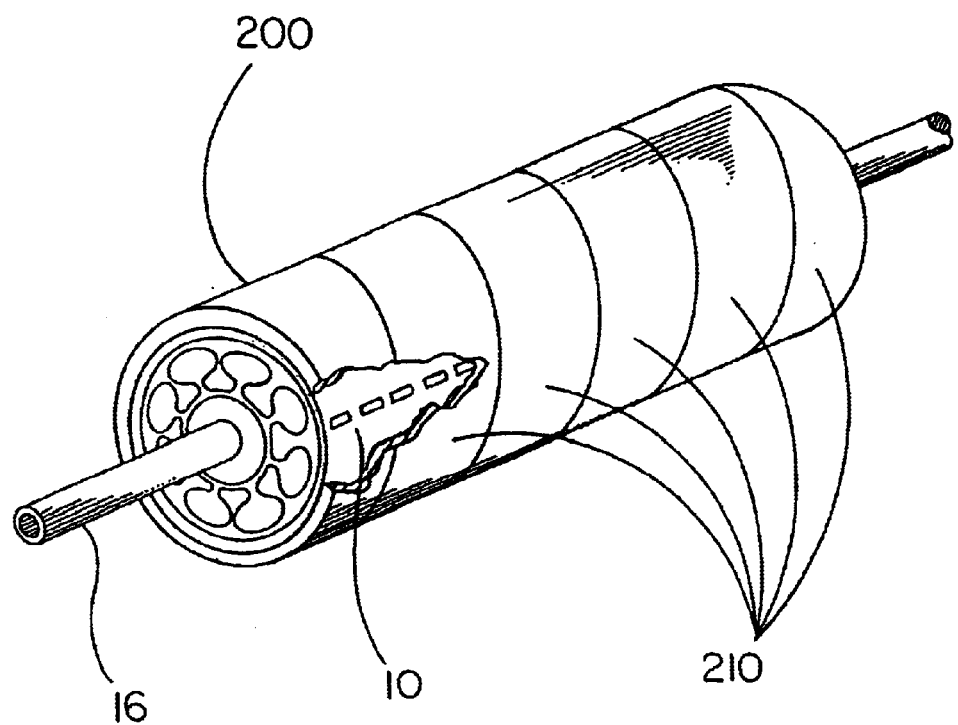
FIG. 20 is a perspective view depicting the packaging sheath configured as a plurality of discrete bands.

FIG. 20 is a perspective view of an alternate embodiment of the packaging sheath 200 wherein the packaging sheath 200 is made up of several bands 210. These bands 210 are to be removed from the constraining sheath assembly 10 one at a time, thus frictional forces are divided by unit number and ultimately are much less than if in performing the same procedure in one continuous length.

Figure 21:
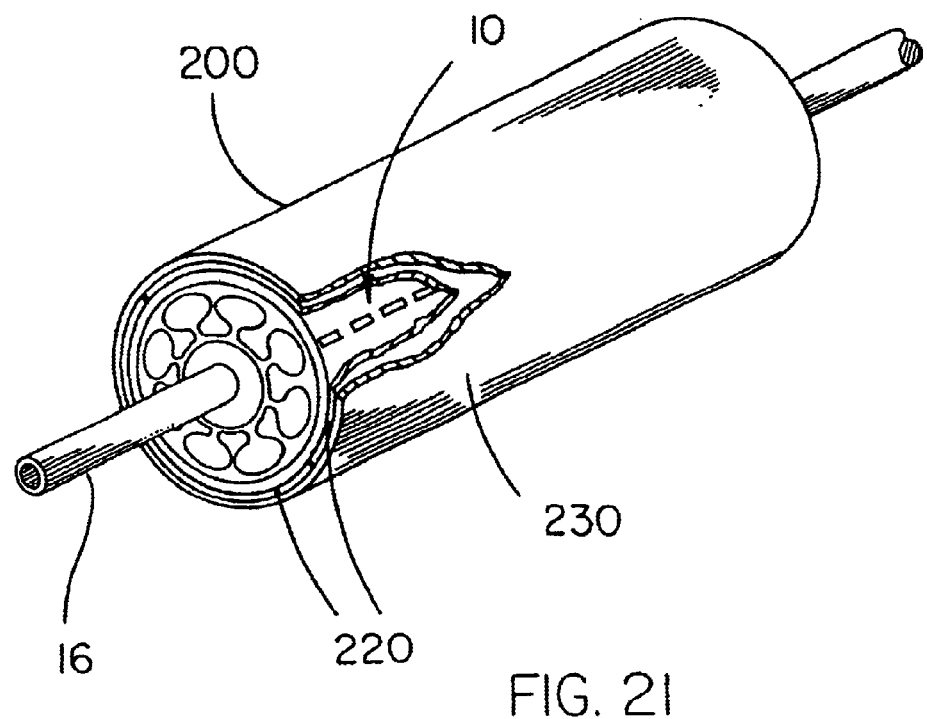
FIG. 21 is a perspective view depicting the packaging sheath configured as a multiple part device.

FIG. 21 is a perspective view of the packaging sheath 200 wherein the constraining sheath 200 is made up of multiple parts 220 and 230. In this configuration, two halves 220 are held together by outer sheath 230 to make up the packaging sheath 200. It should be noted that the "halves" depicted here could be made up of any number of segmental pieces as well as could be a single, split tube with a hinge resembling a "clam shell" type of device.

Figure 22:
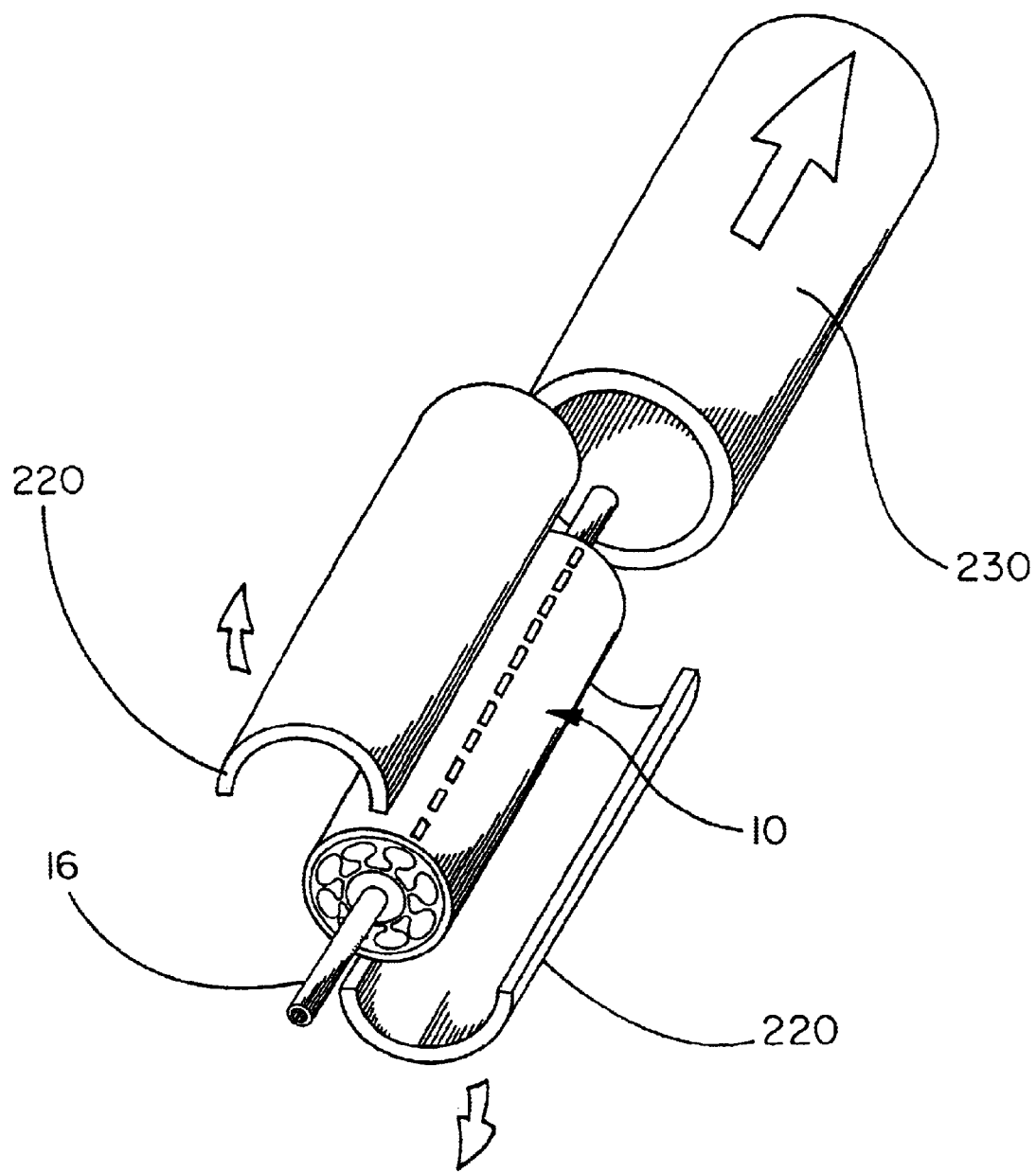
FIG. 22 is an exploded perspective view of the multiple part configuration of the packaging sheath.

FIG. 22 is an exploded perspective view depicting removal of the outer sheath 230 by sliding it axially until it releases the halves 220. The halves 220 then fall apart, exposing the constraining sheath assembly 10 of the present invention. This configuration aids in the prevention of axial displacement of the constraining sheath assembly 10 relative to its deployment balloon.

Figure 23A:
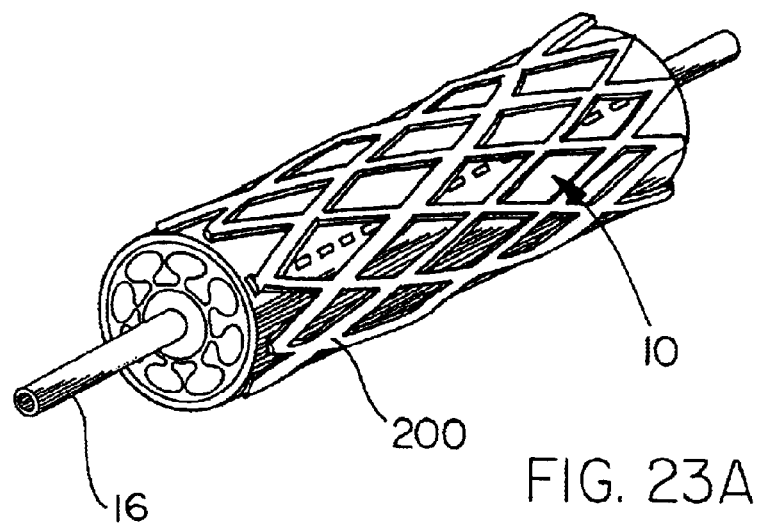
FIG. 23A is a perspective view of a machined tubing, non-continuous configuration of the packaging sheath.
Figure 23B:
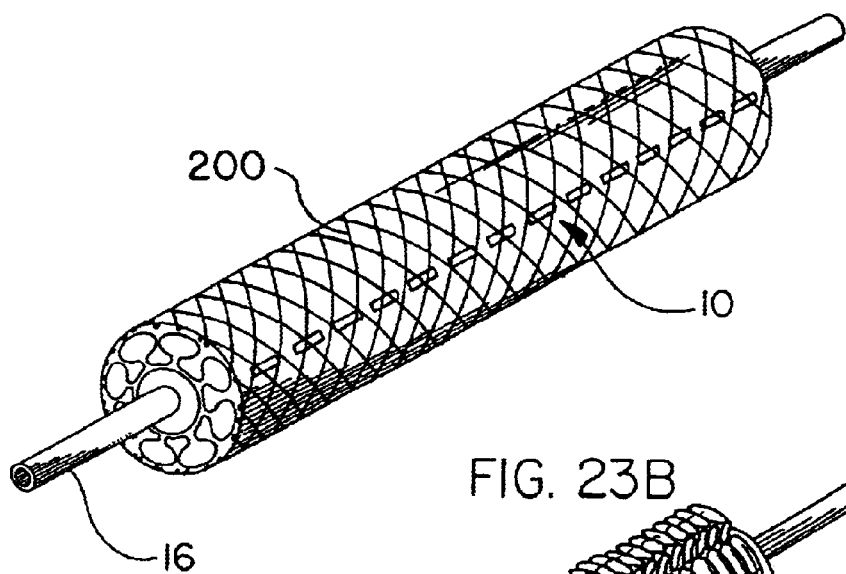
FIG. 23B is a perspective view of a braided filament, non-continuous configuration of the packaging sheath.
Figure 23C:
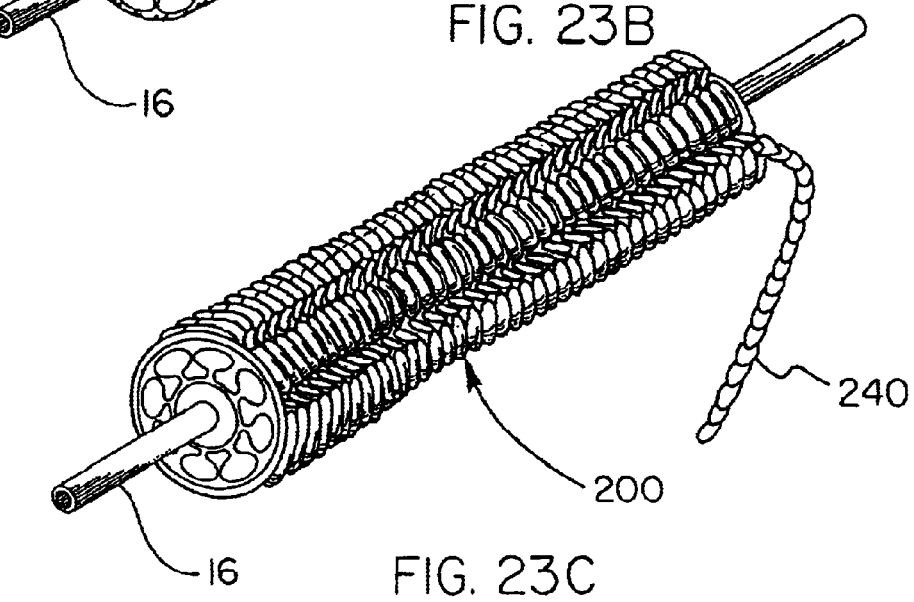
FIG. 23C is a perspective view of a knit-braid, non-continuous configuration of the packaging sheath.

FIGS. 23A through 23C are perspective views of yet other alternative configurations of the packaging sheath 200 wherein an "open mesh" tube is employed to packagingly constrain the constraining sheath assembly 10 of the present invention. Utilizing a tubular device with openings as the packaging sheath 200 is beneficial in that it allows visual inspection of the constraining sheath assembly 10 prior to the packaging processes and can also aid in sterilization. This "open mesh" may be made up of machined, stamped or etched tubing as well as braided, knit or woven metallic or polymeric filaments or a combination thereof and may be removed by sliding it off the constraining sheath assembly 10, by axially shortening the packaging sheath 200 to diametrically enlarge it, or by an unraveling process possible by applying tension to the pull cord 240, or a combination thereof. Such an unraveling tubular knit-braid device as in FIG. 23C is taught in U.S. Pat. No. 6,224,627 to Armstrong et al.

Figure 24:
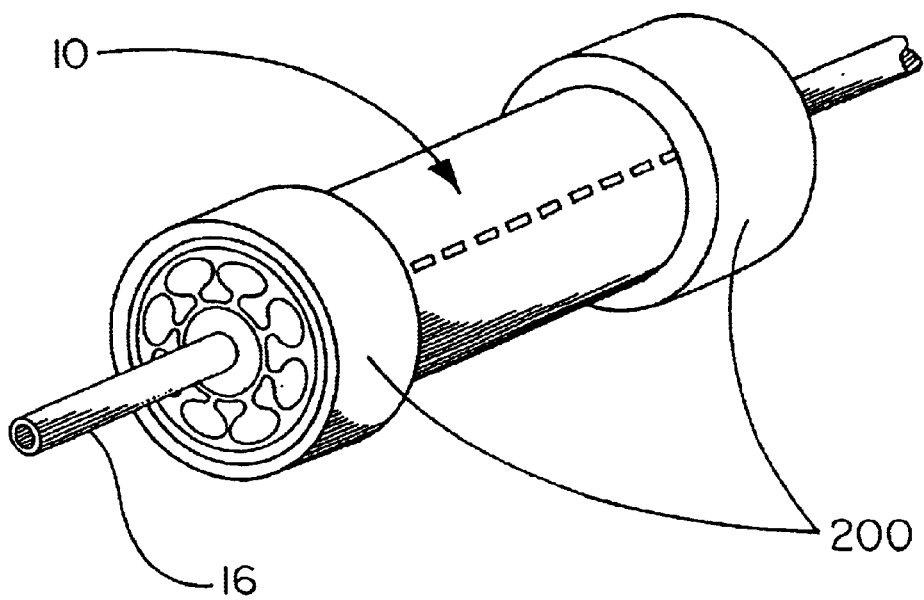
FIG. 24 is a perspective view depicting the packaging sheath configured as a two-part device, with a band at each end of the constrained endoprothesis.

FIG. 24 is used to describe the packaging sheath 200 as two discrete bands placed over either end of the constrained endoprothesis 12. It is typical of helically configured, undulating stent patterns, which terminate in a fashion perpendicular to the stent longitudinal axis (square end) to have varying radial strength within the length of the stent. In this configuration, radial strength at the ends is increased and therefore exerts a higher distension force than at the center portion of the device. This distension force can be contained by the use of one or more packaging sheaths 200.

EXAMPLE 2

Two 4 mm diameter×40 mm length self-expanding endoprostheses were loaded within constraining sheaths constructed as described above, except a 1.6 mm mandrel and a length of 0.04 mm thick×0.4 mm wide gold ribbon were used. To evaluate the necessity of the packaging sheath, the diameters of these assemblies were measured over time without using packaging sheaths in the final device construction. Within 20 minutes after loading the devices within the constraining sheaths, the assemblies (still without packaging sheaths) were conditioned within an oven set at 60° C. and having approximately 15–20% relative ambient humidity within the oven chamber. During exposure to this temperature, periodic diameter measurements were taken. The 60° C. temperature was selected because this is a temperature that the system may be exposed to during a process such as ETO sterilization. Such elevated temperatures can be anticipated to accelerated the disruption or increase in diameter of an endoprothesis assembly including a constraining sheath.

Upon introduction to the chamber, the assemblies had a uniform diameter along their entire length of 1.9 mm. Within 5 hours of exposure, the ends of each device whose constraining sheath had the one less layer had both expanded to an outside diameter as measured by a laser micrometer of 4.0 and 3.3 mm, respectively. The measurement locations were locations marked anywhere near each end of the device and near the middle (three locations). The before-and-after measurements were made at the same locations using an X-Y axis laser micrometer so that six data points resulted. Within 21 hours, greater than 50% of the length of the section of device of both devices with the one extra layer had fully auto deployed to a diameter of 3.8 and 4.1, respectively. Over time, this behavior can compromise endoprosthesis delivery and crossing profiles but it can be prevented by utilization of a packaging sheath that is removed prior to system insertion into the body.

The constraining sheaths used for this example are considered to be "delicate" by virtue of the fact that they either disrupted due to exposure to the increased temperature or increased in diameter by at least 0.15 mm (about one half French size with respect to catheter size units, catheters being available in incremental diameters of one half French). A delicate constraining sheath that increases in diameter by a half French size catheter will thus fit into the next larger French size catheter following this test. A constraining sheath growing this amount will require an increase in one catheter size (by one half French size). A constraining sheath is considered to be a delicate constraining sheath if it disrupts or increases in diameter by at least 0.15 mm (measured as a maximum diameter, meaning the largest diameter obtained when measured with a laser micrometer along the length of the assembly), when exposed to a temperature of 60° C. for a time of 60 days or less, for a time of 45 days or less, for a time of 30 days or less, for a time of 20 days or less, for a time of 10 days or less, for a time of 5 days or less, for a time of 48 hours or less, for a time of 24 hours or less, or for a time of 21 hours or less.

Because the packaging sheath is removed prior to advancing the device into the patient, it is not required to have limitations of profile or biocompatibility necessary for most medical devices inserted within a patient. Therefore, the packaging sheath can be made very strong and designed to retain the auto-expansive forces of the endoprosthesis during sterilization and shelf-life. Upon removal of this packaging sheath, there will be limited time before the endoprosthesis system will distend from auto-expansive forces to a diameter that makes the implantation of the system difficult. The primary constraining sheath should be designed strong enough to resist these auto-expansive forces after the packaging sheath is removed for a reasonable period of time (for example, 5 to 120 minutes). However, the constraining sheath should promptly break when a distending force (e.g. balloon pressure) is applied within the constraining sheath. Without the use of a packaging sheath, these two design requirements are difficult to achieve.

In a further embodiment, in lieu of a packaging sheath, the endoprosthesis assembly of the present invention may be stored and shipped at a temperature less than ambient (i.e., less than 20° C.). A reduced storage temperature for the assembly prior to implantation can also enable the use of a "delicate" constraining sheath without requirement for a packaging sheath. A preferred reduced storage temperature is 5° C. or less. Storage is considered to entail a period of at least 30 days and preferably at least 60 days.

While the principles of the invention have been made clear in the illustrative embodiments set forth herein, it will be obvious to those skilled in the art to make various modifications to the structure, arrangement, proportion, elements, materials and components used in the practice of the invention. To the extent that these various modifications do not depart from the spirit and scope of the appended claims, they are intended to be encompassed therein.

We claim:

1. An endoprosthesis assembly comprising an implantable endoprosthesis capable of being diametrically expanded from a smaller diameter to a larger diameter; and a generally tubular, delicate constraining sheath provided coaxially around the endoprosthesis at the smaller diameter of the endoprosthesis, said constraining sheath being provided with means for disruption initiated by application of a distending force to the constraining sheath, wherein said assembly is contained within a packaging sheath which is not required to be implantable, and wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 21 hours and less than or equal to 60 days.

2. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 24 hours.

3. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 48 hours.

4. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 5 days.

5. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 10 days.

6. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 20 days.

7. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 30 days.

8. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 45 days.

9. An endoprosthesis assembly according to claim 1 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 60 days.

10. An endoprosthesis assembly according to claim 1 wherein the endoprosthesis is a self-expanding endoprosthesis.

11. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 24 hours.

12. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 48 hours.

13. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 5 days.

14. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 10 days.

15. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 20 days.

16. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 30 days.

17. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 45 days.

18. An endoprosthesis assembly according to claim 10 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 60 days.

19. An endoprosthesis assembly according to claim 1 wherein the delicate constraining sheath comprises porous expanded polytetrafluoroethylene.

20. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 24 hours.

21. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 48 hours.

22. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 5 days.

23. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 10 days.

24. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 20 days.

25. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 30 days.

26. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 45 days.

27. An endoprosthesis assembly according to claim 19 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 60 days.

28. An endoprosthesis assembly according to claim 19 wherein the endoprosthesis is a self-expanding endoprothesis.

29. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 24 hours.

30. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 48 hours.

31. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 5 days.

32. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 10 days.

33. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 20 days.

34. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 30 days.

35. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 45 days.

36. An endoprosthesis assembly according to claim 28 wherein the delicate constraining sheath, in the absence of the packaging sheath, either at least partially disrupts or allows an increase in a maximum diameter of the endoprosthesis assembly of at least 0.15 mm, when exposed to a temperature of at least 60° C. for a time of at least 60 days.

* * * * *